(12) United States Patent
Zumpano

(10) Patent No.: US 12,415,145 B2
(45) Date of Patent: *Sep. 16, 2025

(54) COMPOSITIONS THAT CONTAIN LIPOPHILIC PLANT MATERIAL AND SURFACTANT, AND RELATED METHODS

(71) Applicant: Michael V. Zumpano, Fairfield, CA (US)

(72) Inventor: Michael V. Zumpano, Fairfield, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/410,366

(22) Filed: Jan. 11, 2024

(65) Prior Publication Data
US 2024/0189739 A1    Jun. 13, 2024

Related U.S. Application Data

(63) Continuation of application No. 17/459,599, filed on Aug. 27, 2021, now abandoned, which is a (Continued)

(51) Int. Cl.
*A61K 36/185* (2006.01)
*B01D 9/00* (2006.01)
(Continued)

(52) U.S. Cl.
CPC ........ *B01D 11/0288* (2013.01); *A61K 36/185* (2013.01); *B01D 9/0036* (2013.01);
(Continued)

(58) Field of Classification Search
CPC .............. B01D 11/0288; B01D 9/0036; B01D 11/0257; B01D 11/0265; B01D 11/028;
(Continued)

(56) References Cited

U.S. PATENT DOCUMENTS 2,456,097 A    12/1948  Wepplo
3,274,073 A *  9/1966  Burdick ............... C07D 487/22
                                                        435/219

(Continued)

FOREIGN PATENT DOCUMENTS

EP    1480754       4/2010
WO    2016189384   12/2016
WO    2018061009    4/2018

OTHER PUBLICATIONS

Bakkali et al, "Biological Effects of Essential Oils—A Review," Food and Chemical Toxicology. vol. 46, pp. 446-475 (2008).
(Continued)

*Primary Examiner* — Joseph W Drodge
(74) *Attorney, Agent, or Firm* — Dicke, Billig & Czaja, PLLC

(57) ABSTRACT

Described are liquid compositions that contain a desired (e.g., extracted) plant material such as cannabinoid, terpene, terpenoid, or the like, contained, e.g., dissolved, suspended, or emulsified, in the liquid, which contains surfactant; methods of preparing these types of liquid compositions; and methods of processing this type of liquid composition to collect, isolate, concentrate, or purify a desired target material contained in the liquid composition.

13 Claims, 4 Drawing Sheets

Related U.S. Application Data continuation of application No. PCT/US2020/020235, filed on Feb. 27, 2020.

(60) Provisional application No. 62/849,563, filed on May 17, 2019, provisional application No. 62/811,427, filed on Feb. 27, 2019.

(51) Int. Cl.
*B01D 11/02* (2006.01)
*B01D 11/04* (2006.01)

(52) U.S. Cl.
CPC ...... *B01D 11/0257* (2013.01); *B01D 11/0265* (2013.01); *B01D 11/028* (2013.01); *B01D 11/0292* (2013.01); *B01D 11/0492* (2013.01)

(58) Field of Classification Search
CPC ............ B01D 11/0292; B01D 11/0492; B01D 9/0009; B01D 9/0054; B01D 9/0081; B01D 11/0226; B01D 9/00; B01D 9/0059; B01D 9/02; B01D 2009/0086; B01D 11/02; A23L 33/105; A23L 27/11; A61K 36/185; A61K 2236/00; C11B 1/10; C11B 1/108; C11B 3/006; C11B 9/025

See application file for complete search history.

(56) References Cited

U.S. PATENT DOCUMENTS

| | | | |
|---|---|---|---|
| 4,790,666 | A | 12/1988 | Koziol |
| 6,048,836 | A | 4/2000 | Romano et al. |
| 6,172,221 | B1 | 1/2001 | Ruddick |
| 6,481,883 | B1 | 11/2002 | Ellen |
| 7,299,877 | B2 | 11/2007 | Welton et al. |
| 8,523,749 | B2 | 9/2013 | Sudhues et al. |
| 2003/0017216 | A1* | 1/2003 | Schmidt ............... A61K 36/185 424/725 |
| 2008/0169006 | A1* | 7/2008 | Musale ................. B01D 65/02 134/22.19 |
| 2011/0171707 | A1 | 7/2011 | Holt et al. |
| 2011/0282083 | A1* | 11/2011 | Reilly .................. C07C 403/24 549/547 |
| 2014/0328997 | A1* | 11/2014 | Raskin ..................... A23J 3/08 426/657 |
| 2016/0160393 | A1 | 6/2016 | Dhende et al. |
| 2017/0130122 | A1* | 5/2017 | Reyes ..................... C09K 8/035 |
| 2017/0369818 | A1 | 12/2017 | Park et al. |
| 2018/0007924 | A9 | 1/2018 | Goldstein et al. |
| 2018/0042845 | A1* | 2/2018 | Sinai ................... A61K 36/185 |
| 2019/0160393 | A1 | 5/2019 | Marshall et al. |
| 2019/0231833 | A1 | 8/2019 | Garti et al. |
| 2019/0314432 | A1 | 10/2019 | Garti et al. |
| 2020/0246404 | A1 | 8/2020 | Yucel et al. |
| 2020/0315965 | A1 | 10/2020 | Detzel |
| 2022/0047965 | A1 | 2/2022 | Zumpano |
| 2022/0064566 | A1 | 3/2022 | Zumpano |
| 2024/0316132 | A1* | 9/2024 | Zumpano ............... A61K 47/08 |

OTHER PUBLICATIONS

Burke, John, "Solubility Parameters: Theory and Application," The Book and Paper Group, Annual, vol. 3, The American Institute for Conservation, pp. 18 (1984).

Huchelmann et al., "Plant Glandular Trichomes: Natural Cell Factories of High Biotechnological Interest," Plant Physiology, vol. 175, pp. 6-22 (Sep. 2017). <www.plantphysiol.org>.

International Search Report and Written Opinion for International Application No. PCT/US2020/20235 mailed Jul. 2, 2020 (11 pgs).

Bruni, et al., "Cannabinoid Delivery Systems for Pain and Inflammation Treatment," Molecules, vol. 23, 2478, pp. 1-25 (2018).

Triton RW-20 Surfactant, Product Information Page, Dow Surfactants, Dow, Inc., pp. 2, (1995) (retrieved from Internet on Mar. 2, 2023) <https ://www.dow.com/en-us/document-viewer.html?docPath=/content/dam/dcc/documents/en-us/productdatasheet/119/119-02325-01-triton-rw20-surfactant-tds.pdf>.

Stepan, "Steposol MET-10U," Product Bulletin, pp. 3. (2017) (retrieved from Internet on Mar. 2, 2023), <https://www.stepan.com/content/dam/stepan-dot-com/webdam/website-product-documents/product-bulletins/surfactants/STEPOSOLMET10U.pdf>.

"Polysorbate 20," Wikipedia, pp. 3 (2022). <https://en.wikipedia.org/wiki/Polysorbate_20>.

* cited by examiner

COMPOSITIONS THAT CONTAIN LIPOPHILIC PLANT MATERIAL AND SURFACTANT, AND RELATED METHODS

PRIORITY CLAIM

This application is a continuation application of U.S. patent application Ser. No. 17/459,599, filed Aug. 27, 2021, which is a continuation application of PCT/US2020/020235, filed Feb. 27, 2020, which claims the benefit of U.S. Provisional Patent Application Ser. Nos. 62/811,427, filed, Feb. 27, 2019, and 62/849,563 filed May 17, 2019, both entitled "SYSTEM AND METHOD FOR EXTRACTING PLANT LIPOPHILIC MATERIAL", wherein said applications are incorporated herein by reference in their entireties for all purposes.

FIELD

The disclosure relates to liquid compositions that contain a desired plant material such as cannabinoid, terpene, terpenoid, or the like, that is contained, e.g., dissolved, suspended, or emulsified, in the liquid, which contains surfactant; to methods of preparing these types of liquid compositions; and to methods of processing this type of liquid composition to collect, isolate, concentrate, or purify a desired target material contained in the liquid composition.

BACKGROUND

Plant extracts such as essential oils represent a diverse and large collection of natural compounds that are useful for many different purposes. For example, plant essential oils are used for therapeutic, nutritional, cosmetic, food, and flavor and fragrance purposes. Plant essential oils and uses thereof have been reviewed by Bakkali et al. (Food and Chemical Toxicology 46 (2008) 446-475). Therapeutic uses include those such as analgesics, antidepressants, antioxidants, bactericides, virucides, fungicides, and insecticides. Plant essential oils derived from citrus fruits like oranges, lemons, and limes, and from flowering plants such as lavender and rose, are used for flavoring and for imparting desired fragrances and smells to compositions.

Plant essential oils are typically derived from terpenes that are produced by the plant. Terpenes (which includes terpenoids) are derived biosynthetically from units of isopentenyl pyrophosphate ("isoprene"), and are formed using either mevalonate or non-mevalonate pathways in plants. Terpenes encompass a large variety of compounds having isoprene and include hemiterpenes, monoterpenes, sesquiterpenes, diterpenes, sesterterpenes, triterpenes, sesquarterpenes, tetraterpenes, polyterpenes, and norisoprenoids.

Of particular interest are sesquiterpenes such as α-humulene and β-caryophyllene, which provide aroma and flavor of hops, and which affect organoleptic qualities of beer. Cannabis sativa plants also produce a large number of terpenes molecules (including terpenoids), the most notable of which are cannabinoids, which have gained much interest recently due to their therapeutic properties.

Different processes for the extraction of terpenes, such as cannabinoids, from plants are known, but suffer from problems such as inefficiency, poor product recovery, excessive processing times and conditions, use of undesirable, unsafe, expensive, or environmentally unfriendly reagents, and complicated and expensive processing equipment. This area of technology has seen very little success in moving towards more environmentally-friendly processes that recycle materials and produce more eco-friendly waste.

For example, a known process for terpene or cannabinoid extraction is cold pressing for producing hemp seed oil, but this process does not result in an oil high that is high in cannabinoids.

The Rick Simpson Method for Cannabis Oil uses petroleum or naphtha as solvents, but results in products that have a lower concentration of terpenoids and other cannabinoids such as CBD. Further, petroleum or naphtha carried over to the cannabis oil product is undesirable.

Ethanol extraction can be used to extract cannabinoids, but suffers from low selectivity and also pulls in chlorophyll and waxes. Moreover, the use of concentrated ethanol, a flammable liquid, can be undesirable and costly in some instances. Additionally, when ethanol is used as an extraction medium for plant materials such as cannabanoids, the ethanol removes a high amount of waxes from plant material during an extraction step. These waxes must later be removed from the ethanol and the desired plant material. At present, methods of removing waxes from ethanol used as an extraction solvent are costly and complicated, generally involving multiple cycles of freezing the wax out of the ethanol.

Super critical $CO_2$ extraction techniques use solvents, involve complex equipment procedures, and require significant amounts of energy. These methods also require high pressure operating conditions, e.g., sometimes greater than 5000 psi. As such, the cost of the product using such equipment and procedure is high. Further, these techniques require drying the plant, which can be time consuming and also lead to chemical changes in the terpene oils, which are undesirable.

Oil extraction techniques (e.g., using vegetable oils) of terpenoids, while safe, require copious amounts of extraction oil, and can impart undesirable flavors and odors to the terpenoid preparation, which are very difficult to get rid of. Further, cannabinoids quickly degrade in some vegetable oil preparations and therefore it is not used to generate marketable preparations of cannabis oil. Separating cannabinoids from an oil to produce a pure cannabinoid material can be complicated and costly.

Thus, new and more efficient processes are desired for extracting and stabilizing lipophilic phyto-cannabinoids, terpenes, terpenoids, even from newly harvested plant material.

SUMMARY

Described as follows are methods, systems, and compositions useful for extracting desired (target) plant material from a mass of solid plant material that contains the target plant material and non-target plant materials.

The methods and systems include the use of one or more surfactants in a liquid extraction medium, in a chemical extraction process. The surfactant may be a surfactant that is effective to contain (e.g., dissolve, solubilize, suspend, or emulsify) desired target plant material. Examples of these types of surfactant include amide-bases surfactants and "high-KB" surfactants.

The surfactant may alternately or additionally be a "pH-dependent" surfactant, e.g., a nonionic surfactant, that forms an emulsion in a liquid extraction medium at basic pH, and that is de-emulsified at acidic pH.

The surfactant may alternately or additionally be a "detergent" type surfactant, e.g., that improves efficiency or effectiveness of the liquid extraction medium or chemical extraction process.

The liquid extraction medium may optionally include one or more processing ingredients such as: a hydrotrope, a solubilizing agent, chelating agent, sequestering agent, among others, that improve efficiency or effectiveness of the liquid extraction medium or chemical extraction process.

The invention also contemplates plant extract compositions that contain surfactant and target plant material (e.g., target plant compound), as well as methods of processing a plant extract composition to remove, isolate, concentrate, or purify the target plant material. The plant extract composition contains surfactant and plant material (e.g., target plant material, non-target plant material, or both); the plant material may be dissolved, suspended, or emulsified within the plant extract composition. Examples of processing methods include aqueous wash steps, and steps of forming a separate phase of concentrated target plant material from the target plant material contained in a plant extract composition.

In one aspect, the invention relates to a plant extract composition comprising: at least 15 weight percent surfactant, and at least 5 weight percent plant material, based on total weight plant extract composition.

In another aspect the invention relates to a liquid extraction medium that includes water, surfactant, and base. The medium contains: at least 0.1 weight percent pH-dependent surfactant, or at least 1 weight percent amide-based surfactant, or amphiphilic, detergent-type surfactant, or two or more of these, based on total weight liquid extraction medium. The liquid extraction medium has a basic pH.

In another aspect the invention relates to a method of extracting material ("target" material) from solid plant material. The method includes: contacting the solid plant material with liquid extraction medium as described herein to cause the desired (target) plant material to be removed ("extracted") from the solid plant material to become contained in the liquid extraction medium, e.g., dissolved, dispersed, suspended, or emulsified, within the liquid extraction medium.

In another aspect, the invention relates to a method for extracting one or more lipophilic plant materials from a plant (e.g., from solid plant material). The method includes: a) obtaining a plant or portion thereof comprising lipophilic plant material; b) processing the plant in an aqueous composition, wherein the aqueous composition has a basic pH and comprises at least one surfactant; c) lowering the pH of the aqueous composition wherein the surfactant i) partially or fully loses its ability to emulsify lipophilic and hydrophilic components in the processed plant composition, ii) partially or fully disassociates with the lipophilic plant material, iii) is chemically cleaved into two or more surfactant by-product, or any combination of i)-iii); and d) partially or fully separating the surfactant from the lipophilic plant material.

In another aspect the invention relates to a system for extracting a lipophilic plant material from a plant. The system comprises: a) a plant processor cable of processing the plant using pressure, and in an aqueous composition comprising a surfactant; b) a pH-lowering feature, capable of lowering the pH in the aqueous composition; and c) a separator, capable of separating the surfactant from the lipophilic plant material.

In another aspect, the invention relates to a use of a multi-stage auger for removing liquid components from solid plant material.

In another aspect, the invention relates to a chemical extraction system as described herein, e.g., that includes an electrolysis unit, and methods of processing a liquid composition using the electrolysis unit.

Figure 1:
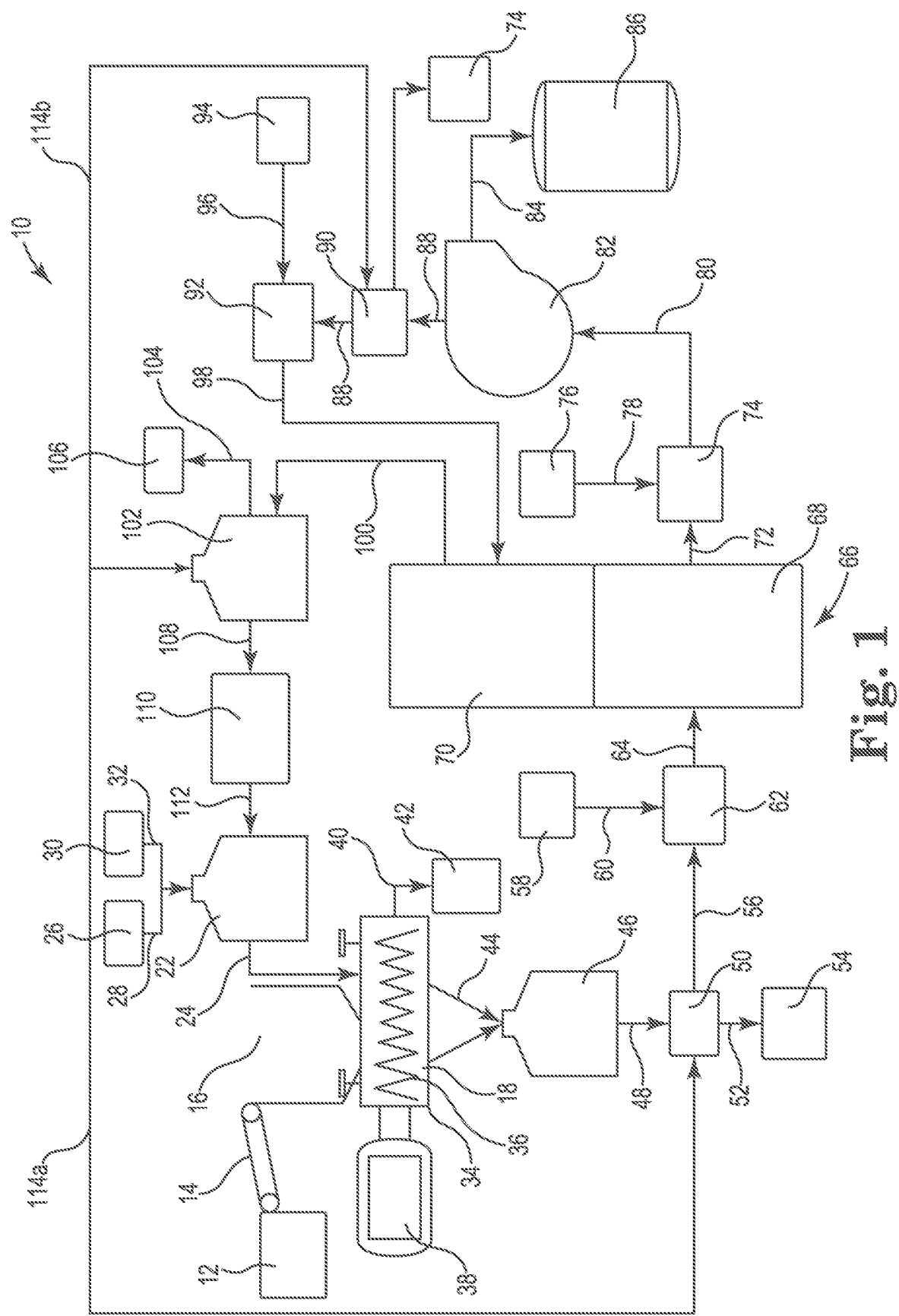
FIG. 1 is an illustration of a system for processing plants and extracting lipophilic plant material therefrom according to an embodiment of the disclosure.

All figures are not to scale, and are schematic.

DETAILED DESCRIPTION

The following description relates to methods and systems for extracting desired (target) plant material from a mass of solid plant material that contains the target plant material and non-target plant materials; to compositions (e.g., liquid extraction mediums) used in the methods and systems; to compositions derived from the methods, including plant extract compositions and derivatives thereof; to methods of processing plant extract compositions derived from the methods of extraction, e.g., to isolate and purify target plant materials; and to compositions that contain isolated and optionally concentrated amounts of target plant materials in surfactant.

A plant extract composition is a liquid solution that contains a concentrated amount of one or more desired ("target") plant materials dissolved, suspended, or otherwise contained in a liquid that contains surfactant. As determined by the Applicant, certain types of surfactants can exhibit an ability to contain a useful or advantageous amount of organic materials, generally lipophilic materials, derived from a plant. Previous to the present invention, surfactants in the absence of or in the presence of only a low amount of organic solvent or an oil, have not been considered useful as an extraction medium into which such plant materials can be dissolved, suspended, or otherwise contained, for processing, e.g., by chemical extraction methods or subsequent collection, isolation, and concentrating steps. Certain examples of surfactants that have now been identified as being capable of containing useful amounts of dissolved plant materials, e.g., lipophilic plant materials, without the need for organic solvent or oil, are surfactants that include an amide functionality, surfactants that have a relatively high Kauri-butanol (KB) value, and surfactants that exhibit both of these properties. Other surfactants useful in liquid extraction mediums include pH-dependent surfactants, and "detergent-type" surfactants.

The plant extract composition can be produced by any useful technique. As described herein, example techniques include chemical extraction processes that chemically extract (remove) a desired (target) plant material, which is generally considered to be a lipophilic material, from solid plant material by steps that include allowing or causing the target plant material to become contained in, e.g., dissolved, emulsified, dispersed, or suspended in, a liquid extraction medium or a portion thereof.

The liquid extraction medium can include one or more types of liquid surfactants that effectively function to allow the liquid extraction medium to contain target plant material in a liquid form, as a dissolved, suspended, dispersed, or emulsified material within the liquid extraction medium. The liquid extraction medium can be prepared to contain one or all of these ingredients before the liquid extraction medium is applied to the solid plant material.

In other methods, one or more of the ingredients of the liquid extraction medium may be applied to solid plant material at different times, e.g., sequentially and in any order. For example, surfactant of a liquid extraction medium may be applied to the solid plant material before water, or water may be applied to the solid plant material before surfactant, as desired. Additional processing ingredients may be applied with surfactant, water, both, or neither. Regardless of the order or number of steps used to apply ingredients of a liquid extraction medium to a mass of solid plant material, the total amount of the different ingredients that are added to the solid plant material, e.g., at a stage of processing, is considered to constitute a liquid extraction medium.

Alternately or additionally, certain example chemical extraction methods include surfactant, referred to as "conditional" or "switchable" surfactant, that exhibits properties that can be substantially changed during processing. An example is a "pH-dependent" surfactant, which exhibits varied surface active functionality (e.g., formation of micelles) in a liquid extraction medium, depending on a pH condition of the liquid extraction medium.

Example plant extract compositions (e.g., plant extract solutions) can be in the form of a liquid combination of two or more liquid substances that include one or more surfactants and the target plant material suspended, emulsified, or dissolved within the composition. A plant extract composition may optionally, additionally contain an amount of non-target plant materials, which are also generally lipophilic, depending on a degree of processing of the plant extract composition, such as between the plant extract composition being included in a liquid extraction medium, and the plant extract composition being a downstream composition that has been processed to remove or eliminate portions of non-target plant material for the purpose of isolating or concentrating the target plant material.

Example plant extract compositions can be liquid compositions as described, that contain a target plant material, or a combination of at least the two different types of plant materials, one of which is a target plant material. Some specific examples of plant extract compositions are liquid combinations that include: the target plant material and optional non-target plant materials, either or both of which may be liquid materials; surfactant (e.g., "high KB" surfactant, which acts as a solvent to dissolve, suspend, emulsify, or otherwise contain the target plant material, "pH-dependent" surfactant, "detergent-type" surfactant); and other optional ingredients such as an amount of water, or small or minor amounts of one or more additional processing ingredients such as organic solvent, oil, acid, base, chelating agent, hydrotrope, solubilizing agent, anticorrosion agent, etc., as described herein.

In some examples, a plant extract composition may contain a substantial amount or an excess amount of surfactant (e.g., at least 1, 5, 10, 15, 20, 30, or 50 weight percent) that is effective as a solvent for dissolving, suspending, emulsifying, or otherwise containing target plant material, and a useful amount of the target plant material contained in the plant extract composition, such as at least 1, 3, or 5 weight percent target plant material based on total weight plant extract composition.

As used herein, the terms "solvent," "solution," and "solute" are given a meaning that is consistent with the uses of these terms within the chemical arts: e.g., a "solution" can be a homogeneous liquid mixture of two or more miscible substances, including a solvent and a solute; the substance in which the solute is dissolved is called a solvent; the substance dissolved in the solvent is the solute.

The terms "solvent," "solution," and "solute," though, also more generally are given a meaning associated with a range of liquid compositions that are combinations of two or more different miscible or non-miscible liquid materials, such as suspensions, emulsions, and microemulsions, even if the liquid composition is not technically or positively a "solution" of solute dissolved in solvent. A "solution" according to this generalized meaning may be homogeneous or non-homogeneous on a macroscopic scale, and may be homogenous or non-homogeneous at a microscopic level. Examples of such "solutions" may contain micelles or momentarily suspended fine droplets of one liquid within another liquid. The droplets or micelles may allow or cause the liquid to be translucent, clear, or cloudy.

Also as used herein, the term "composition" refers generally to a range of liquid compositions that contain two or more liquids, with the composition being a "solution" as described, an emulsion, a microemulsion, a suspension, or another form of liquid. A liquid composition may contain two or more liquid materials that may be miscible or non-miscible, such as surfactant and target plant materials, e.g., a "plant extract composition" as described, with one of the liquid materials being contained in the other liquid material in any manner, e.g., suspended (as microscopic or macroscopic droplets), as a solute dissolved in solvent, or as a component of an emulsion or a microemulsion, etc. Example "compositions" may also contain suspended solids, multiple phase, e.g., of an emulsion, and may be clear, translucent, colored, or cloudy.

In these or other example plant extract compositions, the target plant material may exist as a liquid that is miscible with, dissolved within, suspended in, or emulsified within the composition, with a substantial amount of surfactant included in the plant extract composition. The target plant material and the surfactant, with either of these being present in an amount greater than the other, may exist as a single phase or multiple phases that contains the two liquid materials.

A plant extract composition as described may exist as a single phase, e.g., consist of or consist essentially of the composition itself with no other solid or liquid component present in combination with the single phase solution. Alternately, the composition may contain one or more additional solid or liquid material such as water phase that may be present as a separate phase. In this state, the multi-phase composition may be processed, e.g., by a method of the present description, to separate a non-aqueous phase that contains target plant material from an aqueous phase, and to further remove the desired target plant material from the non-aqueous.

As used herein the term "surfactant" refers to organic chemical compounds generally and specifically described herein, and that are generally capable of lowering the surface tension of water. Surfactant compounds may be categorized into at least five different classes of surfactant compounds, which include: cationic surfactants, anionic surfactants, amphoteric surfactants, zwitterionic surfactants, and non-ionic surfactants, and include surfactants of the present description referred to as "high KB" surfactants, amide-based surfactants, "pH-dependent" surfactants, and detergent-type surfactants.

A surfactant useful in a composition or method of the present description can be chemically different from non-surfactant processing liquids that are considered to be effective to dissolve target plant materials in chemical extraction methods, including methods for extracting cannabinoids. Various such currently- or previously-used processing liquids include organic solvents, oils, or both, that have been used in previous chemical extraction techniques including but not limited to ethanol extraction techniques, supercritical $CO_2$ extraction techniques, and oil extraction techniques. Examples of the organic solvents and oils used in these techniques include ethanol, vegetable oils, as well as others. See, e.g., United States Patent Publication 2019/0231833.

Surfactants that are useful or preferred for methods or compositions of the present description include surfactant compounds that can be included in a liquid extraction medium of a chemical extraction process either alone or in combination with one or more additional processing ingredients (e.g., water, base, another surfactant or surfactants) exogenous to the plant and added to the process to effect or facilitate removal of an endogenous target plant material from the solid plant material. Examples of exogenous processing ingredients include exogenous water, exogenous organic solvent, exogenous oil, another chemical surfactant, exogenous acid or base, exogenous buffer, with these processing ingredients being included in a liquid extraction medium that is capable of containing (e.g., dissolving, suspending, emulsifying) a desired amount of one or more target plant materials (e.g., cannabinoid).

Surfactant of example plant extract compositions may become a liquid component of the plant extract composition due to use of the surfactant as a liquid component of a process used to prepare the plant extract composition. For example, a surfactant of a plant extract composition may be one that was included as a component of a liquid extraction medium during a chemical extraction process.

Surfactant that may be useful in a liquid extraction medium may be included for one of various different purposes within the liquid extraction medium. Certain example surfactants may be included in a liquid extraction medium for a purpose of acting as a "solvent" that is effective to dissolve, emulsify, or suspend a desired endogenous target plant material to facilitate removing the target plant material from a mass of solid plant material during the extraction process. Alternately or additionally, different surfactants types may be included in a liquid extraction medium for a purpose of acting as an emulsifier in the liquid extraction medium, to selectively produce an emulsion or a non-emulsion, to facilitate processing of the liquid extraction medium during the extraction process.

Additionally, liberation of target material from a plant material may be facilitated by a temperature of the liquid extraction medium that is in excess of the melting point of certain target materials. For example, the melting point of CBDA is in excess of 60C. Extraction of target materials may be improved by maintaining contact of plant material and a liquid extraction medium at a temperature of at least 65C along with a useful amount of shear or compression creating by agitation, pressure pumping such as with a cavity pump or auger, sonication or any useful method of shear mixing. Such shear or compression may also serve to break plant material, exposing more surface to liquid extraction medium, thereby improving extraction.

Examples of useful or preferred liquid extraction mediums may be made substantially or mostly of surfactant and water with a relatively low amount of other ingredients that include optional processing aids (base, chelating agents, a hydrotrope, an organic solvent, an oil, a buffer, a corrosion inhibitor, a solubilizing agent, among others), exogenous organic solvent, or exogenous oil. According to certain examples, a liquid extraction medium (before being applied to solid plant material) may be made substantially or mostly of water and surfactant (e.g., as described herein, e.g., pH-dependent surfactant, high KB surfactant, amide-based surfactant, a "detergent"-type surfactant, or two or more of these), e.g., may contain at least 50, 60, 70, 80, 90, or 95 weight percent combined amounts of water and surfactant, based on total weight liquid extraction medium.

According to these and other examples, a liquid extraction medium may be made of water and non-water components (i.e., all materials that are not water), with the non-water-components being substantially, predominantly, or mostly surfactant, e.g., one or a combination of surfactants as described. For example, total non-water components of an example liquid extraction medium (before being applied to solid plant material) may be made substantially, predominantly, or mostly of surfactant (e.g., as described herein, e.g., pH-dependent surfactant, high KB surfactant, amide-based surfactant, "detergent-type" surfactant, or two or more of these), e.g., may contain at least 20, 30, 40, 50, 60, 70, 80, or 90 weight percent surfactant, based on total weight liquid extraction medium.

Examples of useful amounts of water (from any source) contained in a liquid extraction medium, e.g., before being applied to solid plant material or at a stage of processing, and which may be an emulsion (including microemulsions) that contains an aqueous phase and a non-aqueous phase, as described, can be an amount of water in a range from 5 to 95 percent by weight, e.g., from 10 to 90, from 15 to 80, or from 20 to 70 percent by weight based on total weight extraction medium. In certain example processes, water may be incorporated into the liquid extraction medium by combining an amount of water with other processing ingredients of the extraction medium, such as one or more surfactants, an acid or base, chelating agent, etc., and forming an emulsion that is then applied to or contacted with solid plant material. Amounts of water may be contained in one or more of the solid plant material or a processing ingredient (e.g., as part of a commercial surfactant product that contains surfactant molecules with water or another solvent); any water contained in another ingredient of a liquid extraction medium, or as part of the solid plant material, that becomes part of the liquid extraction medium, is included in the above ranges.

A useful liquid extraction medium may also contain amounts of one or more other optional exogenous processing ingredients such as exogenous water, exogenous oil, exogenous organic solvent, additional surfactant or emulsifier, chelating agent, corrosion inhibitor, a pH buffer, hydrotrope, solubilizing agent, optional acid or base, among others. In certain example liquid extraction mediums and methods, a liquid extraction medium does not require and may specifically exclude, or may use a low or a limited amount of any added (exogenous) oil, added (exogenous) polysaccharide, added (exogenous) carbohydrate, or added (exogenous) organic solvent.

The amounts of exogenous oil and exogenous organic solvent in example liquid extraction mediums may be relatively low, according to these example methods, due possibly in part to a high effectiveness of a surfactant that is included in the extraction medium for the purpose of dissolving, suspending, or emulsifying the target plant molecule. Certain preferred extraction mediums of the present description do not require and may specifically exclude or contain not more than an insubstantial or low amount of exogenous organic solvent, exogenous oil, or both, for example may contain less than 1, 0.5, 0.1, 0.05, or 0.01 weight percent exogenous organic solvent, exogenous oil, or a combination of these, based on total weight extraction medium.

A material that is referred to herein as "endogenous" is a material that is naturally part of a chemical makeup of plant material, such as water, oils, chlorophylls, plant fiber, etc., that are naturally present in the plant material before the plant material is processed by a chemical extraction step.

A liquid extraction medium may include a pH buffer to improve operating efficiency of a chemical extraction method. Chemical conditions of a liquid extraction medium may vary during a course of an extraction process due, for example, to a changing or varied composition of solid plant material that is being supplied to the extraction process. The chemical makeup of the solid plant material entering the extraction process may vary in terms of the amount of water contained in the plant material, the amount of target and non-target plant materials, and in terms of the amounts of different chemical constituents of the solid plant material that affect or buffer pH during processing. A pH buffer may be added to the liquid extraction medium as a processing ingredient for the purpose of stabilizing the pH of the liquid extraction medium during processing.

In a liquid extraction medium, alkalie can be useful to soften plant material and improve penetration of a liquid extraction medium. Alkalie can liberate phytol from chlorophyll to produce a cationic or base chlorophyllide such as sodium chlorophyllide. Alkalinizing the liquid extraction medium may also increase solubility of certain target materials such as acid cannabinoids and certain carboxylated terpenoids.

Buffers may be used to maintain a useful pH and also to prevent escalation of pH that might damage certain target materials. For example, KOH in the presence of oxygen may convert certain acid cannabinoids, including CBDA, to a quinone or hydroquinone form, by adding oxygen to the phenol ring of CBDA. According to certain example methods and liquid extraction mediums, a liquid extraction medium (before being combined with plant material) can contain a blend of two different buffers, e.g., sodium carbonate and sodium bicarbonate, to buffer around a particular range, such as to a pH in a range from 10 to 11. To the liquid extraction medium may then be added an alkalie such as LiOH, KOH or NaOH, or any alkali metal hydroxide or ammonium hydroxide, to raise the pH to a higher level (e.g., from 11 to 12) that will maintain the liquid at a pH of approximately 10 after interaction with the plant matter.

Examples of useful pH buffers include sodium carbonate, sodium bicarbonate, and the like. Useful examples of buffer salts can also reduce the solubility of a target material, e.g., cannabinoid, in a water phase of a liquid extraction medium, thereby causing the target plant material to be thermodynamically driven into a non-aqueous phase of a liquid extraction medium, resulting in a higher concentration of target plant material in the non-aqueous phase.

In example liquid extraction mediums, a chelating agent may be included to sequester certain types of materials, including heavy metals, pesticides, herbicides, and the like. An example of a chelating agent is disodium-EDTA.

In example liquid extraction mediums, a salt or other ionic material or other chemical agent may be added in an amount that is effective to drive target plant material out of an aqueous phase and into an oil phase. Examples of such salts may include NaCl, KCl, LiCl, $NaBH_4$, sodium hexametaphosphate, among others.

Alternately or in addition, example liquid extraction mediums may include a corrosion inhibitor, an oxidation inhibitor, or both, e.g., sodium borohydride ($NaBH_4$).

Alternately or in addition, example liquid extraction mediums may include a solubilizing agent to increase partitioning of sparingly water-soluble lipophilic components into a lipophilic phase. A solubilizing agent (or "solubilizer") is capable of being dissolved in water or a water phase, to attract a lipophilic plant material, e.g., one or more non-target compounds. Propylene carbonate (PC), for example, has about 24% solubility in water. A liphophilic target compound such as CBDA is not attracted to a solubilizer, but non-target compounds such as surfactant (e.t., Met10U) may be attracted to the solubilizing agent and can be drawn into the water. Consequently, a solubilizer may be useful to remove some non-target compounds from an oil phase of an emulsion or other composition and to move the non-target compound into an aqueous phase. Additionally, a solubilizing agent (e.g., propylene carbonate) may attract other compounds such as chlorophyll (pheophorbide, pheophytin, chlorophyllide and many other derivatives of chlorophyll) to allow cleaning of the non-aqueous phase to remove those color components from target compounds such as acid cannabinoid extracts.

Certain examples of solubilizing agents include alkylene carbonates such as propylene carbonate, ethylene carbonate, and glycerol carbonate; glycerol; alkylene glycols such as propylene glycol; and mixtures thereof, such as a combination of propylene glycol (5 to 40 parts by weight) and glycerol carbonate (95 to 60 parts by weight).

An amount of one or more solubilizing agents included in a liquid extraction medium may be from 0 to 20 weight percent, for example from 1 to 5, 10, or 15 weight percent, based on total weight liquid extraction medium.

One type of example surfactant that may be included in a liquid extraction medium is a surfactant that facilitates removing (extracting, suspending, emulsifying, or dissolving) endogenous target plant material from a mass of solid plant material during an extraction process by being capable of containing a relatively high amount of target plant material, e.g., in a dissolved, suspended, or emulsified state, such as by forming particles or micelles that contain the target plant material. In the past, chemical extraction methods have been designed and performed by contacting an organic solvent or a liquid oil with solid plant material that contains endogenous target plant material, and causing target plant material to become dissolved or otherwise contained in the organic solvent or liquid oil. Organic solvents useful in these processes have generally included solvents and oils (which are lipophilic) that are known or expected to be capable of dissolving a high amount of organic material, especially lipophilic plant materials. Examples of liquids previously used as extraction solvents include non-surface-active organic compounds such as ethanol, vegetable oils, mineral oil, hexane, toluene, acetone, among others.

In contrast to previous chemical extraction methods, methods and compositions of the present description do not require an organic solvent of the type that is typically considered to be effective for dissolving organic materials. Example plant extract compositions as described herein, as well as liquid extraction mediums that may (in example methods) be used to produce the plant extraction solution, may instead be prepared and used based on a determination, made by the Applicant, that liquid surfactants, i.e., a class of organic chemicals that are not typically considered to be "organic solvents" known for an ability to dissolve useful amounts of organic material, are in fact effective for the purpose of containing target plant materials (e.g., by dissolving, suspending, or emulsifying) when extracting various target plant materials from solid plant material, even in the absence of organic solvent, oil, or water, or in combination with only a small or minor amount of organic solvent, oil, or water. In this sense, the surfactant may be considered to function as a "solvent" in an extraction medium, by causing removal of the target plant material from solid plant material by dissolving, suspending, or emulsifying the target plant material.

As determined by the Applicant, certain types of surfactants, in the absence of organic solvent, oil, or both, or in combination with a low or minor amount of either or both, can exhibit an ability to dissolve, suspend, emulsify, or otherwise contain useful or advantageous amounts of organic materials, generally lipophilic materials, derived from a plant. Previous to the present invention, surfactants have not been considered useful to function as an extraction medium (e.g., a "solvent" of an extraction medium, into which organic materials generally, or plant materials specifically, can be effectively dissolved, suspended, or contained, for processing, in the absence of a significant or major amount of organic solvent or oil. The present description relates to the Applicant's novel and inventive understanding that a surface active compound, e.g., surfactant, can be effective for this function, particularly to remove desired plant materials such as lipophilic compounds, e.g., terpenes, cannabinoids, other oils, etc., from a solid plant material, in the absence of organic solvent, or oil, or in combination with a low or minor amount of organic solvent, oil, or both.

Advantageously relative to previous extraction processes for removing cannabanoids from plant material, which at the same time remove a high amount of wax from the plant material and require complicated processes of removing wax from the ethanol, surfactants of the present description (e.g., "high KB" surfactants and amide-based surfactants) are capable of removing useful or advantage amounts of target plant materials from a mass of solid plant material, but do not remove wax in an amount that requires complicated and costly processing steps for the specific purpose of removing the wax from the surfactant in a downstream step.

Certain examples of surfactants that have been identified by the Applicant as being capable of containing (e.g., dissolving, suspending, or emulsifying) useful or advantageous amounts of these types of plant materials for processing include: surfactants that contain an amide functionality, surfactants that have a relatively high Kauri-butanol value, or both.

The Kauri-Butanol test is a "cloud-point" test for ranking hydrocarbon solvent strength. The kauri-butanol value (KB) of an organic material represents the maximum amount of that material that can be added to a stock solution of kauri resin (a fossil copal) in butyl alcohol without causing cloudiness. Because kauri resin is readily soluble in butyl alcohol but is relatively less soluble in other hydrocarbon solvents, the kauri resin solution will tolerate only a certain amount of dilution. "Stronger" solvents such as toluene can be added in a greater amount (and thus have a higher KB value) compared to "weaker" solvents like hexane. See, Burke, John "Solubility Parameters: Theory and Application," The Book and Paper ANNUAL, Vol. 3., The American Institute for Conservation (1984).

KB values are not a typical or conventionally-referenced property of surface active chemical compounds of the type generally used as a surfactant based on a surface active property of the compound. These types of compounds are not typically considered for use in a capacity as a "solvent" to dissolve a "solute" of a chemical extraction process. KB values are more typically considered to be informative for selecting organic compounds normally used as a "solvent," for a purpose of dissolving a useful (e.g., substantial) amount of a solute. The present Applicant, however, has determined that surface active compounds ("surfactants," herein) that may be useful in a chemical extraction method or as part of a composition as described (e.g., a liquid extraction medium, a plant extract composition, or a derivative of one of these), for a purpose of removing and containing target plant material from solid plant material, may possess a relatively high KB value. To the Applicant's understanding, previous uses of KB values for selecting an organic liquid for use as a solvent (for any given use or solute) have not included consideration of a KB value for selecting a surface active compound (which compounds are not even necessarily understood to function as "solvents") for use as a solvent in a chemical extraction processes, as described herein.

Preferred surfactant selected to function as a solvent to contain (e.g., dissolve, suspend, or emulsify) target plant material in a chemical extraction method as described, particularly a lipophilic plant material, e.g., a terpene or a cannabinoid, can have a KB value of at least 100, for example at least 150, 200, 300, 500, 700, 900, or 1000. A surfactant such as this, that exhibits a KB value of at least 100, may sometimes be referred to herein as a "high KB surfactant."

For comparison, various organic solvents that are commonly used or recognized as effective for the specific purpose of dissolving a solute (e.g., for processing, cleaning, etc.) and that have KB values below 150 include: ethanol (having a KB value of 130), benzene and toluene (each having a KB value below 110), xylene (having a KB value below 100), cumene (having a KB value below 90), cyclohexane and turpentine (each having a KB value below 60), ethyl cyclohexane (having a KB value of about 50), and heptane, pentane, and hexane (each having a KB value below 30).

Certain example surfactants that have been identified by the Applicant as being useful or preferred for use in a method or composition as described, capable of containing (e.g., by suspending, emulsifying, or dissolving) a useful or advantageously high amount of target plant material, particularly a lipophilic plant material, e.g., a terpene or a cannabinoid, include amide-based surfactants, e.g., tertiary amides, including amide-based or tertiary amide surfactants that have a high KB value.

General examples of amide-based surfactants that may be useful in a method or composition as described include surfactants that have the formula $R^4C(O)NR^5R^6$, wherein $R^4$, $R^5$, and $R^6$ are independently selected from saturated and unsaturated hydrocarbon-containing groups. In example amide-based surfactants, $R^4$, $R^5$, and $R^6$ can have a total number of carbon atoms in the range of about 6-16, 8-14, or 10-12. For example, an amide-based surfactant can be of the following formula:

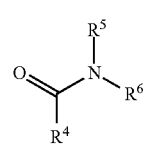

wherein $R^4$ is a saturated or unsaturated alkyl chain, $R^5$ and $R^6$ are the same or different and are saturated alkyl chains, wherein $R^4$ has a greater number of carbon atoms than $R^5$, $R^6$, or each one of $R^5$ and $R^6$ independently. Examples of useful or preferred amide-based surfactants can include di-methyl amides, wherein each of $R^5$ and R is a methyl group. According to these and other examples, $R^4$ may preferably be a straight alkyl group that is saturated or unsaturated, and that has from 7 to 20 carbon atoms, e.g., from 8 to 15 carbon atoms.

According to certain examples, a useful amide-based surfactant may be selected from: N,N-dimethyl 9-decanamide (DMDA), N,N-dimethyldecanamide (DMDAA) (a.k.a. N, N-dimethylcapramide), dimethyl lauramide, N,N-dimethyl-dodecanamide, N,N-dimethylmyristamide, and N,N-dimethyldecanamide. A preferred amide-based surfactant is N, N-dimethyl 9-decenamide (Steposol™ MET-10U, Stepan Co., Northfield, IL). STEPOSOL™ MET-10U has a very high Kauri-butanol value (greater than 1000); a boiling point of 297° C.; and formulating pH range of 3-12:

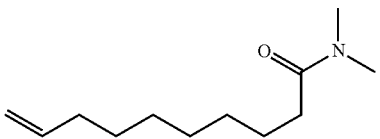

An alternate preferred amide-based surfactant is N, N-dimethyldecanamide (N, N-dimethylcapramide) (commercially available from Stepan Co. as HALLCOMID® M-10), which has a KB value of about 300.

An alternate useful or preferred amide-based surfactant is NINOL CAA (N,N-diemethyl[lauramide/myristamide]).

One or more additional features of a useful or desired high KB surfactant or amide-based surfactant can be: a low solubility of the surfactant in acidic water (e.g., water having a pH below 7, 6, 5, or 4) water; an ability to hold a useful amount of dissolved water; or both. According to useful or preferred examples, a high KB surfactant or an amide-based surfactant can have a solubility in acidic water that is less than 1 weight percent, e.g., less than 0.5 weight percent or less than 0.25 weight percent (solubility of the surfactant in water at 25 degrees Celsius). If present in an acidic water phase of a liquid extraction medium or a derivative thereof, this type of surfactant can attract target plant material and draw the target plant material into the water phase. A lower solubility of this surfactant in the acidic water will reduce the amount of the surfactant in an acidic water phase of a liquid extraction medium, which will in turn reduce the amount of target plant material in the water phase.

Alternately or in addition, a high KB surfactant or an amide-based surfactant may also have an ability to contain dissolved water at a maximum amount that is not more than 25 weight percent (water dissolved in the surfactant at 25 degrees Celsius), e.g., a maximum solubility of water in the surfactant in a range from 0.5 to 10, or from 1 to 10, 15, 20, or 25 weight percent dissolved water per total weight surfactant.

Examples of useful amounts of surfactant that may be included in a liquid extraction medium for a purpose of containing (e.g., by dissolving, suspending, or emulsifying) an amount of target plant material (e.g., a "high KB surfactant" or an amide-based surfactant) can be an amount in a range from 0.1 to 20 percent by weight, e.g., from 1 to 10 percent by weight, or from 2 to 8 percent by weight based on total weigh liquid extraction medium (which includes water and non-water components).

Separately or in combination with surfactant that is effective to contain a useful or advantageous amount of target plant material, e.g., terpene, cannabinoid, etc., example liquid extraction mediums as described may alternately or additionally contain an additional surfactant that is effective to act as an emulsifier to selectively form an emulsion at high pH, that may be de-emulsified to form a non-emulsion at lower pH, to facilitate processing of the liquid extraction medium during or subsequent to the chemical extraction step. These surfactants, capable of selectively being emulsified and de-emulsified based on pH, may be referred to herein as "pH-dependent" surfactants, and are chemically not identical to a surfactant added to a liquid extraction medium or a plant extract composition for the purpose of containing target plant material; examples of pH-dependent surfactants, for example, are not amide-based surfactants or high KB surfactants.

During one or more steps or portions of a chemical extraction method, or in a subsequent processing step, a liquid extraction medium or a plant extract composition may take the form of an emulsion (including microemulsions). Emulsions are well understood multi-phase liquid compositions, and are sometimes classified as a Windsor Type I, Type II, Type III, or Type IV emulsion, based on phase equilibria. In a Type I emulsion, the surfactant is preferentially soluble in water and the emulsion is an oil-in-water (o/w) form (Winsor I). The surfactant-rich water phase coexists with the oil phase where surfactant is only present as monomers at a small concentration. In a Type II emulsion, the surfactant is mainly in the oil phase and the emulsion is a water-in-oil (w/o) form. The surfactant-rich oil phase coexists with the surfactant-poor aqueous phase (Winsor II). In a Type III emulsion, a three-phase system exists where a surfactant-rich middle-phase coexists with both of excess water and oil phases that are surfactant-poor. In a Type IV emulsion: the liquid is a single-phase (isotropic) micellar solution. Depending on surfactant type and sample environment, types I, II, III or IV form preferentially, the dominant type being related to the molecular arrangement at the interface.

A pH-dependent surfactant may be effective to selectively form a stable (for purposes of processing as described herein) emulsion based on a pH condition. Such surfactants are functionally sensitive to a pH shift that can be produced during or subsequent to processing of plant material by a chemical extraction process. In particular, at an elevated pH, such as above 7, above about 7.5, and preferably above about 8.0, above about 8.5, above about 9.0, such as in the range of about 9.0 to about 13, or about 10 to about 13, a pH-dependent surfactant is able to: a) emulsify lipophilic (non-aqueous) and hydrophilic (aqueous) components of a liquid extraction medium, b) promote association of a surfactant (e.g., a high KB surfactant) with target plant material or lipophilic plant material, c) maintain the chemical integrity of the pH-dependent surfactant, or any combination of a)-c). Accordingly, the elevated pH condition facilitates action by the pH-dependent surfactant (e.g., the surfactant is "functionally active") to form an emulsion for processing the plant material and liquid extraction medium during steps of a chemical extraction method as described.

In one or more subsequent steps of a chemical extraction method as described, the pH of the processed plant composition and liquid extraction medium can be lowered, thereby affecting the functionality of the pH-dependent surfactant. In particular, at a lowered pH, such as at 7 or below, below 7, at a pH in the range of about 1 to 7, and preferably below about 6.5, below about 6.0, such as in the range of about 3.0 to about 6.0, the pH-dependent surfactant: a) partially or fully loses its ability to emulsify lipophilic and hydrophilic components in the processed plant composition, including the liquid extraction medium, b) partially or fully disassociates with the lipophilic plant material, c) is chemically cleaved into two or more surfactant by-products, or any combination of a)-c). Accordingly, a lowered pH condition of the liquid extraction medium partially or fully prevents surfactant action for forming an emulsion (e.g., the surfactant is "functionally inactive"). The liquid extraction medium is no longer emulsified by the pH-dependent surfactant and the liquid extraction medium will separate into two phases, including an aqueous phase and a non-aqueous (e.g., "oil") phase.

A useful or preferred pH-dependent surfactant can be chosen and used in an amount to cause a liquid extraction medium to form an emulsion at a condition of basic pH. Formation of the emulsion can effectively separate desired target and non-target plant material (e.g., lipophilic plant material, terpenes, cannabinoids) present in a non-aqueous (oil) phase of the emulsion, from an aqueous phase of the emulsion that contains lower amounts of the target plant material and non-target lipophilic plant material.

During processing, the emulsion is de-emulsified or "broken" by reducing the pH of the liquid extraction medium that is in the form of an emulsion. After the emulsion is "broken," the liquid extraction medium forms separate phases that include an aqueous phase and a non-aqueous (oil) phase. The non-aqueous phase can include: surfactant as described, including one or more of: surfactant that acts as a "solvent" for dissolving, emulsifying, suspending, or otherwise containing target plant materials (e.g., high KB surfactant or amide-based surfactant); pH-dependent surfactant; and "detergent-type" surfactant; target and non-target plant materials dissolved in the non-aqueous phase; and optional amounts of exogenous processing ingredients that are miscible with, dissolved, or otherwise contained in the non-aqueous phase, e.g., dissolved water, dissolved or miscible additional surfactant, dissolved or miscible exogenous oil, dissolved or miscible exogenous organic solvent, acid, base, and other exogenous processing ingredients such as chelating agent, solubilizing agent, hydrotrope, etc.

The non-aqueous phase can preferably contain a useful or relatively high concentration of dissolved plant material, e.g., dissolved lipophilic plant materials that include target plant material, non-target plant material, a combination of various lipophilic plant materials, etc. Examples of useful non-aqueous phases are capable of containing from 0.1, up to or in excess of 1, 3, or 5 weight percent, or up to or in excess of 10, 20 30, 40, or 50, 70, or 90 weight percent dissolved plant material (e.g., target plant material and non-target plant material), based on total weight of the non-aqueous phase of the liquid extraction medium. Preferred non-aqueous phases may contain least at least 1, 2, 3, or 5, and up to or in excess of 10, 20 30, 40, 50, 60, or 70 weight percent dissolved target plant material (e.g., cannabinoid, terpene) based on total weight of the non-aqueous phase.

According to these or other embodiments, a useful or preferred non-aqueous phase may contain a relatively low amount of water, exogenous oil, and exogenous organic solvent. The non-aqueous phase may contain dissolved water in an amount in a range from 1 to 20 weight percent, e.g., from 2 or 5, up to 15 weight percent (e.g., at 70 degrees Fahrenheit) of the non-aqueous phase. The non-aqueous phase may contain surfactant (of one or more types described herein) in an amount in a range from 15 to 90 weight percent surfactant, in a range from 20 to 90 weight percent, or from 30 to 80 weight percent surfactant, based on total weight of the non-aqueous phase. Example non-aqueous phases may contain exogenous oil, exogenous organic solvent, or a combination of these, in an amount that is less than 5, 2, 1, 0.5, or 0.1 weight percent.

By use of the pH-sensitive surfactant, methods and compositions as described allow for efficient (and preferably rapid) de-emulsification of the stable emulsion. Reducing pH of the emulsion (i.e., of the liquid extraction medium) deactivates the pH-dependent surfactant to cause de-emulsification of the liquid extraction medium that causes the liquid extraction medium to separate into a liquid composition that contains at least two phases that include at least an aqueous phase and a non-aqueous phase. The non-aqueous phase (which may be considered a "plant extract composition" as described herein) can be further processed to remove, isolate, collect, or purify target plant material contained therein.

Examples of useful amounts of pH-dependent surfactant that may be included in a liquid extraction medium can be present in any amount that is effective to form an emulsion at a basic pH and to become de-emulsified at an acidic pH. Functionally, this requires an amount of the pH-dependent surfactant in a liquid extraction medium that is at least an amount of a critical micelle concentration. Examples of numerical ranges may be in a range from 0.01, 0.1, 1, or 2, up to 40 percent by weight, e.g., from 1 to 30 percent by weight, or from 5 to 20 percent by weight based on total weigh liquid extraction medium.

Examples of pH-dependent surfactants include non-ionic surfactants that are effective for pH-dependent formation and de-formation of an emulsion, in a liquid extraction medium, as described. A method and system of the present description may use, e.g.: a single non-ionic surfactant as part of a liquid extraction medium for processing the plant material; a liquid extraction medium that contains a combination of two or more different non-ionic surfactants; or a liquid extraction medium that contains a combination of at least one non-ionic surfactant and one or more surfactants that are different from the non-ionic surfactant, such as an anionic surfactant and/or a cationic surfactant, as well as an amid surfactant or "high KB" surfactant as described herein, to dissolve or otherwise contain target plant material.

Optionally, as an alternative to a pH-dependent surfactant, a method may include forming a temporary suspension by mechanical action, as opposed to a chemical surfactant, such as by use of sonication or homogenization. In example such methods, a liquid extraction medium does not require and may substantially exclude any amount of pH-dependent surfactant, e.g., may contain less than 0.1, 0.01, 0.001, or less than 0.0001 weight percent pH dependent surfactant, will contain a high-KB or an amide based surfactant, and before being applied to solid plant material may be formed into a temporary suspension by ad sonicating or homogenizing step.

In example embodiments, a method or system of the disclosure may use a non-ionic, pH-dependent surfactant that includes one or more of the following chemical features: a nitrogen (N) atom; a sulfur atom (S), an oxygen atom (O), a hydrocarbyl group (e.g., alkyl); an ether group; or an alkoxy group. In certain examples, a method or system of the disclosure may use a non-ionic surfactant that includes: a nitrogen atom, an alkyl group, and an ether group. Certain examples of non-ionic surfactants of the disclosure include alkylamine alkoxylate surfactants.

Exemplary alkylamine alkoxylates (tertiary amines) include those that have the formula $R^1NR^2R^3$, wherein $R^1$ is a hydrocarbon-containing group, and $R^2$ and $R^3$ are independently selected from groups that include both oxygen and carbon atoms. For example, $R^1$ has an amount of carbon atoms in the range of 6-24, preferably 8-18, or preferably 12-14, and $R^2$ and $R^3$ are independently selected from alkoxylate groups, and preferably both $R^2$ and $R^3$ are alkoxylate groups. Preferred non-ionic surfactants are alkylamine ethoxylates, such as those prepared under the tradename Triton™ RW (Dow Chemical Company). Exemplary alkylamine ethoxylates can be represented by the following formula:

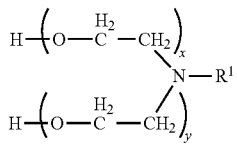

wherein $R^1$ is an alkyl group having a number of carbons in the range of about 12 to about 14, and wherein x and y are each independently one or more, and preferably the sum of x and y is in the range of 2 to about 20, or 2 to about 15.

Triton™ RW surfactants include RW-20 (2 moles ethylene oxide (2 M EO); HLB: 6-8); RW-50 (5 M EO; HLB: 12-14); RW-75 (7.5 M EO; HLB: 14-16); RW-100 (10 M EO; HLB: 16); RW-150 (15 M EO; HLB: >16). At elevated pH conditions (>7, >8, >9) the alkylamine ethoxylate exists substantially in the free-amine form and functions as a nonionic surfactant. Addition of a hydrogen ion (by lowering the pH) can change the surfactant chemistry, see, for example, U.S. Pat. No. 7,299,877. Other examples of useful non-ionic surfactants include surfactants sold under the trade name Toximul®, such as Toximul CA-2 and CA-7.5 ethoxylated coco amine surfactants.

In one example, a single alkylamine ethoxylate having HLB of about 16 or greater (e.g., Triton™ RW-100 or RW-150) may be used in a liquid extraction medium, such as in an amount in the range of about 0.1, 0.5, 1, or 2% (wt) to about 10, 15, or 20% (wt) based on total weight liquid extraction medium.

Examples of useful or preferred pH-sensitive surfactants may be capable of being emulsified at a high pH, subsequently de-emulsified by reducing pH of the emulsion, and then preferably separated from the emulsion and re-used in the upstream chemical extraction process. The pH-sensitive surfactant may become included in the aqueous phase of a de-emulsified liquid composition. The aqueous phase may then be separated from the non-aqueous phase of the de-emulsified composition, and the aqueous phase may be processed to remove salts from the liquid by passing the aqueous phase through a deionization (DI) system, allowing for recovery and re-use of the pH-sensitive surfactant.

In some example embodiments, two surfactants, or more than two surfactants, are used as pH-dependent surfactants in a liquid extraction medium, such as two non-ionic surfactants. For example, an example liquid extraction medium can include a first pH-dependent surfactant and a second pH-dependent surfactant, wherein one or both of the first and second pH-dependent surfactants are active to form an emulsion at a basic pH, and inactive at an acidic pH. The first and second pH-dependent surfactants can be selected from alkylamine ethoxylates (Triton™ RW-series surfactants) such as those described herein. The first pH-dependent surfactant can have a different hydrophilic/lipophilic balance (HLB) compared to the second surfactant, and can be used in a different amount in a liquid extraction medium as compared to the second surfactant. For example, a first pH-dependent surfactant can have a lower HLB than a second pH-dependent surfactant and the second surfactant may be present in the liquid extraction medium in an amount (weight or weight percent) that is greater than that of the first surfactant.

A combination of two or more different pH-dependent surfactants can be chosen based on the HLB of a desired target material in the plant, such as depending on a pH at which a stable emulsion will form by using at least two surfactants, e.g., one surfactant having a HLB above that of the target compound and one surfactant having a HLB below that of the target compound. Accordingly, in modes of practice the methods of the disclosure can include a) identifying one or more target lipophilic materials in the plant and obtaining information of the HLB of the one or more target lipophilic materials, b) selecting a first pH-dependent surfactant that has a HLB that is less than the one or more target lipophilic materials, c) selecting a second pH-dependent surfactant that has a HLB that is greater than the one or more target lipophilic materials, and d) using the first and second surfactants as part of a liquid extraction medium to process the plant material.

For example, a liquid extraction medium can include a first pH-sensitive surfactant (e.g., alkylamine ethoxylate) having a HLB of about 16 or greater (e.g., Triton™ RW-100 or RW-150) that is used in an amount that is greater than a second pH-sensitive surfactant (e.g., alkylamine ethoxylate) having a HLB of less than 16 (e.g., Triton™ RW-50), or less than 10 (e.g., Triton™ RW-20). In particular examples, the first alkylamine ethoxylate with the higher HLB may be used in an amount in the range of about 2% (wt) to about 20% (wt) of the liquid extraction medium, and the second alkylamine ethoxylate with the lower HLB is used in an amount in the range of about 0.1% (wt) to about 10% (wt) of the liquid extraction medium. The use of the second pH-dependent alkylamine ethoxylate surfactant with the lower HLB can enhance separation of a target plant material, e.g., lipophilic plant material such as cannabinoids, from other components of the liquid extraction medium, e.g., from an aqueous phase or fraction into an oil phase that contains high KB surfactant. Further, the second alkylamine ethoxylate may remain in contact with a target plant material such as a cannabinoid, e.g., CBD (CBD in a pure state is a solid crystal) when the pH of the liquid extraction medium is lowered and the first alkylamine ethoxylate with higher HLB is inactivated, and this in turn promotes enhanced separation of the cannabinoid from the aqueous fraction. Even further, the use of the second alkylamine ethoxylate can also protect target plant material such as cannabinoid from irreversible chemical changes during processing.

Advantageously, according to certain specific example methods and compositions of the present description, a high KB surfactant as described may be useful in combination with one or more pH-dependent surfactants, especially to extract cannabinoids, to improve extraction efficiency compared to using only a pH-dependent surfactant or a high KB surfactant. For example, using only pH-dependent surfactant (one or a combination of two or more pH-dependent surfactants), an extraction efficiency may be in a useful range, such as from 50 to 70 percent. (Extraction efficiency refers to an amount of target material removed from solid plant material compared to total target material in the solid plant material at a start of an extraction process, on a percentage basis.) Using a blend of two or more pH-dependent surfactants with a high KB surfactant (e.g., an amide-based surfactant) can improve efficiency relative to using only pH-dependent surfactants, e.g., to an efficiency of at least 80 percent, such as from about 80 to 85 percent. In other examples, a liquid extraction medium that contains a single pH-dependent surfactant and a small amount of high KB surfactant (equal to cannabinoid content by weight of the solid plant material) may result in up to or above 80, 90, 95, or 98 percent extraction efficiency.

Optionally, a liquid extraction medium can include a surfactant that is different from a pH-dependent non-ionic surfactant, and that is also different from a high KB surfactant and an amide surfactant. For example, a liquid extraction medium or a derivative thereof can include a pH-sensitive surfactant (e.g., alkylamine ethoxylate), a high KB or amide surfactant, or both, as described herein, in combination with an anionic or cationic surfactant. Alternately, or additionally, a liquid extraction medium may include first and second pH-dependent (e.g., alkylamine ethoxylate) surfactants such as described herein in combination with an anionic or cationic surfactant. Exemplary cationic surfactants include phosphonium, sulfonium, and mono- or tri-long chain quaternary ammonium surfactants, such as alkyltrimethylammonium chlorides. Exemplary anionic surfactants include water-soluble salts of fatty acid monoglyceride monosulfates, alkyl sulfates such as sodium lauryl sulfate, alkyl aryl sulfonates such as sodium dodecyl benzene sulfonate, alkyl sulfoacetates, such as sodium lauryl sulfoacetate (dodecyl sodium sulfoacetate), fatty acid esters of 1,2 dihydroxy propane sulfonate, sulfocolaurate (N-2-ethyl laurate potassium sulfoacetamide) and sodium lauryl sarcosinate.

Separately or in combination with other surfactants, example liquid extraction mediums as described may alternately or additionally contain surfactant that is of a type that is known to be effective as a detergent, i.e., a "detergent-type" surfactant.

Detergent-type surfactants are generally understood to be amphiphilic compounds that have cleansing properties in dilute solutions. These types of surfactants may be cationic, anionic, or non-ionic forms. They may be interchangeably referred to as detergents or surfactants.

Examples of detergent-type surfactants include but are not limited to: zwitterionic surfactant compounds; betaines and other quaternary ammonium surfactants; sodium laureth sulfate—in the class of anionic detergents; sodium caprylyl sulfonate (SCS)—anionic; sodium alkane sulfonate (a general class) of which SCS is part; alkylbenzenesulfonates; dimethyl lauramide/myristmide (a tertiary amide with a mixture of R=C11 and C13; dodecyl benzene sulfonic acid—very acidic anionic surfactant with a SO3H head instead of an amide; cationic surfactant that include benzalkonium chloride, dimethyldioctadcylammonium bromide (these are quaternary ammonium compounds (cationics can be used in the process as a phase transfer agent); Olafur (this compound includes a fluoride ion associated with each of two +N—H moieties and is not a quaternary ammonium); tetramethylammonium hydroxide +N—(CH3)4-OH, which is a very strong base.

An amount of detergent-type surfactant, e.g., alkylbenzenesulfonate surfactant, in a liquid extraction medium can be any useful amount, e.g., any amount that will facilitate a chemical extraction process to remove target compound from solid plant material and allow or cause the target compound to become present in an oil phase of a liquid extraction medium. Examples of numerical ranges may be in a range from 0.1 to 40 percent by weight, e.g., from 1 to 30 percent by weight, or from 5 to 20 percent by weight detergent-type surfactant based on total weigh liquid extraction medium.

Example liquid extraction mediums as described may alternately or additionally contain a hydrotrope. A hydrotrope is a compound that solubilizes hydrophobic compounds in an aqueous solution. Typically, a hydrotrope compound includes or consists of a hydrophilic part and a hydrophobic part, but the hydrophobic part is generally too small to cause spontaneous self-aggregation, e.g., the formation of micelles. A hydrotrope may be amphiphilic in the case of sodium xylene sulfonate, or non-amphiphilic in the classic case of urea (urea is polar in the same sense that water is polar, but is not truly amphiphilic in the sense that urea also has a strictly nonpolar group). Thiourea is also an example of a hydrotrope. Hydrotropes commonly are distinguished as not having the non-polar chain length to allow true micelles to form. Some compounds that are contain a chain having a length of 5 or 6 carbon may form micelles, and others may not; many hydrotropes do not have a carbon chain of greater than 5 or 6 carbons in length.

Hydrotropes are characterized as having a non-linear concentration-solubility curve. For many hydrotropes a 2.0 molar solution results in high solubility (at least 90 percent of a maximum solubility) of a compatible compound, where dilution to 0.6 molar solution or below results in very low solubility (a few percent of a maximum solubility). According to these examples, a three-times dilution (dilution of one volume of solution or emulsion with three volumes of water) causes more than an order of magnitude reduction in solubility of the compound.

Examples of hydrotrope compounds include amphiphilic compounds having: an alkyl chain that may be cyclic, pi-bonded cyclic (aromatic), phenolic, short alkane, or a combination of these; and an opposite end (head) that may be a sulfate, sulfonate, amine, or amide. Specific examples of compounds include: xylene sulfonate (e.g., sodium xylene sulfonate), cumene sulfonate, toluene sulfonyl (CH3C6H4SO2->R(O2)-S-Benzene-CH3). Examples of non-amphiphilic hydrotropes include urea (O—(NH2)2) and thiourea (S—C—(NH2)2).

An amount of hydrotrope included in a liquid extraction medium may be any amount that is effective for performing or improving efficiency of an extraction process as described. Examples of numerical ranges may be any range that produces a molar concentration of at least 2.0M in an aqueous phase of a liquid extraction medium, although other amounts may also be useful and effective.

With respect to using an exogenous oil as part of an extraction medium, the term "oil" refers to natural or synthetic organic compounds that are generally non-surface active, non-amphiphilic, that can be used are in liquid form at a process temperature (which may be higher than room temperature), that are considered to be hydrophobic and lipophilic. Typical examples of exogenous oils include petroleum-based oils, animal-based oils, plant-based oils, and derivatized versions thereof (e.g., alkylated counterparts). Specific examples include paraffinic oils, essential oils, mineral oil, vegetable oil, biodiesel, methylated seed oil, castor oil, olive oil, soybean oil, canola oil, cotton oil, palmolein, sunflower oil, corn oil, isopropyl myristate, oleyl lactate, coco caprylo caprate, hexyl laurate, oleyl amine, oleic acid, oleyl alcohol, linoleic acid, fish oil, ethoxylated oil, peptoil crop oil concentrate, DEG crop oil concentrate, crop oil (petroleum) concentrate, and the like.

As described, the use of an exogenous oil in an extraction medium may be considered useful in various extraction processes (see United States Patent Number 2019/0231833). And while a liquid extraction medium of the present description may optionally contain an amount of exogenous oil, other examples of useful or preferred liquid extraction mediums of the present description do not require an exogenous oil, may use an amount of exogenous oil that is relatively low, or may avoid the use of exogenous oil. Examples of useful amounts of exogenous oil in a liquid extraction medium can be an amount in a range from 0 to 50 percent by weight, e.g., from below 1 or 1 to 15, from 5 to 10 or from 10 to 50 percent by weight, based on total weight liquid extraction medium. Certain preferred extraction mediums of the present description do not require and may specifically exclude exogenous oils, for example may contain less than 1, 0.5, 0.1, 0.05, or 0.01 weight percent exogenous oil based on total weight extraction medium.

Examples of exogenous oils that may be included in a liquid extraction medium, optionally in a limited or low amount, or that may be excluded from a liquid extraction medium, include fatty acids, fatty acid esters, seed oils, petroleum oils, fatty alcohols, fatty ethers, fatty amides, and glycerides, among others, including the following (some of these may also be endogenous to a solid plant material, in which case the oil is not considered exogenous):

Fatty acid esters have the general formula:

$$R'C(O)\text{---}O\text{---}C_nH_{2n+1}$$

wherein $R^1$ is an alkyl radical having from about 4 to about 22 carbon atoms, and n is a number from 1-4, e.g., n=1 for a fatty acid methyl ester and n=2 for a fatty acid ethyl ester. Common methyl esters include methyl oleate, methyl laurate, and methyl soyate. Common ethyl esters include ethyl oleate and ethyl canolate. Suitable fatty acids from which the fatty acid esters may be derived include, but are not limited to, coconut, soy and other vegetable oils, tallow, etc. Alkoxylated fatty acid esters include fatty acid esters such as those listed above, and that are alkoxylated with ethylene oxide, propylene oxide, and combinations thereof. Fatty alcohols include saturated or unsaturated, branched or linear $C_8$-$C_{20}$ alcohols, e.g., $C_8$-$C_{20}$ alcohols. Fatty acids include those that have an alkyl group with from 4 to 22 carbon atoms, and a terminal carboxyl group. The fatty acid may be saturated such as, for example, butyric, lauric, palmitic, and stearic, or unsaturated such as, for example, oleic, and linolenic.

Seed oils include those derived from vegetables, seeds, and nuts, and include, but are not limited to, castor oil, coconut oil, soybean oil, vegetable oils, and the like. Soybean oil can be processed further to produce methylated or ethylated seed oils, commonly referred by the abbreviations MSO and ESO. MSOs and ESOs can be produced by hydrolysis (cleaving) of the glycerol molecule from the fatty acids. The fatty acids are then separated from the glycerol molecule and other water soluble components and esterified with methanol (to produce MSO) or ethanol (to produce ESO).

Petroleum oils include, but are not limited to, petroleum and petroleum-derived oils such as mineral oil.

Essential oils include R-limonene, D-limonene, terpenes, mineral oil, paraffinic oils, phospholipids, polar lipids (squalenes, spingomelines), waxes, vegetable oils, triglycerides, glycerides, fatty acids and esters of fatty acids, liquid hydrocarbons, and others, and any mixture thereof. Specific examples include medium-chain triglycerides (MCT), olive oil, soybean oil, canola oil, cotton oil, palmolein, sunflower oil, corn oil, isopropyl myristate, oleyl lactate, coco caprylocaprate, hexyl laurate, oleyl amine, oleic acid, oleyl alcohol, linoleic acid, linoleyl alcohol, ethyl oleate, hexane, heptanes, nonane, decane, dodecane, triacetin, neem oil, lavender oil, peppermint oil, anise oil, menthol, capsaicin, grape seed oil, pomegranate oil, avocado oil, sesame oil, fish oil, omega oils and omega fatty acids, and similar essential oils and mixtures thereof.

With respect to exogenous organic solvents, the term "solvent" or "organic solvent" refers to compounds that are non-surface active, i.e., that are different from surfactants as described herein. While the use of an exogenous solvent in an extraction medium may be considered useful in various extraction processes (see United States Patent Number 2019/0231833), and while a liquid extraction medium as described may optionally contain an amount of exogenous solvent if desired or useful, certain examples of useful or preferred extraction mediums of the present description do not require exogenous solvent, or may use an amount of exogenous solvent that is relatively low. Examples of useful amounts of exogenous solvent in an extraction medium can be an amount in a range from 0 to 20 percent by weight, e.g., from 1 to 15, from 5 to 10 or from 10 to 50 percent by weight. Certain preferred extraction mediums of the present description do not require and may specifically exclude or contain not more than an insubstantial or low amount of exogenous organic solvent, for example may contain less than 1, 0.5, 0.1, 0.05, or 0.01 weight percent exogenous organic solvent based on total weight extraction medium.

As used herein, the term "solvent" or "organic solvent" refers to an organic compound, different from an oil and different from a surfactant as described herein (e.g., an organic solvent is generally non-surface active and non-amphiphilic), which is miscible in the liquid extraction medium and together with surfactant and water of a liquid extraction medium may form a liquid extraction medium or a portion of a liquid extraction medium (e.g., homogenous liquid or liquid phase of an extraction medium) that dissolves the target plant material, e.g., CBD. An organic solvent may, according to some embodiments, be selected from liquid hydrocarbons such as alcohols and others. According to some examples, organic solvent that may be included in a liquid extraction medium, or alternately excluded from a liquid extraction medium or used in a liquid extraction medium at a low or limited amount, may be ethanol, propanol, isopropanol, other short-chain alcohols, acetic acid, lactic acid, fumaric acid, malic acid, tartaric acid, succinic acids, polyols, glycerol, xylitol, as well as others.

Typical steps of a chemical extraction process may include a step of mechanically processing an amount of solid plant material, and a step (optionally in combination with the mechanical processing step) of chemically extracting endogenous target plant material, normally along with an amount of endogenous non-target plant material, from the mechanically processed plant material or a derivative thereof. The mechanical processing and chemical extraction process may be performed by any useful mechanical processing and chemical extraction techniques, in a useful sequence. The steps can include contacting the solid plant material with a liquid extraction medium as described herein (or individual components of a liquid extraction medium), e.g., that contains: a non-aqueous phase that contains one or more surfactants, dissolved water, and other dissolved exogenous processing ingredients or dissolved ingredients such as acid, base, hydrotrope, solubilizing agent, and (while not required or necessarily preferred) an amount of dissolved exogenous oil, dissolved exogenous organic solvent, or two or more of these. If a sufficiently high amount of water is combined with the non-aqueous phase, the liquid extraction medium can be in the form of a multiple-phase liquid that includes the non-aqueous and an aqueous phase that is made mostly of water, e.g., as multiple phases of an emulsion.

Mechanical processing may involve any step of mechanically converting solid plant material into smaller sized pieces or particles, such as by grinding, augering, cutting, etc., as well as by squeezing or pressing to remove liquid contents of the solid plant material. Chemical extraction steps can involve any types of chemical processing to separate one or more desired target plant materials from solid plant material or from undesired impurities (e.g., undesired or "non-target" plant materials, fiber, etc.). Such chemical processing may include heat (high temperature), and contact with a liquid extraction medium that contains a surfactant that acts as a solvent to the target plant material, e.g., that dissolves the target plant material; the liquid extraction medium may also contain an amount of optional dissolved water, optional exogenous organic solvent, optional exogenous oil, optional exogenous sequestering agents, optional exogenous chelating agents, optional exogenous acid or base, optional hydrotrope, optional solubilizer, optional buffer, optional oxidization inhibitor, optional corrosion inhibitor, optional coagulant, optional flocculant, etc., to facilitate removal by extraction of the target plant material during contact with the liquid extraction medium, to facilitate preservation or processing of target materials, to facilitate conversion or removal of non-target materials, to facilitate purification upon extraction of target or non-target materials, to facilitate recovery of extraction components such as the high-kB surfactant, switchable surfactant, or other materials, to facilitate safety or disposal features of the above as well as of effluent waste materials that may enter the environment.

The mechanical processing step, chemical extraction step, and other optional steps, will produce a plant extract composition that contains liquid material of an oil phase of the liquid extraction medium (containing one or more surfactants). The plant extract composition will contain a concentrated amount of target plant material, non-target plant materials, and possibly an amount of dissolved water.

The target plant material can be obtained from any plant type. A "target plant material" may be any endogenous plant material (i.e., a material that is naturally part of the chemical makeup of the plant material) that is desirably removed from the solid plant material and isolated or concentrated for a useful purpose. A purpose of the target plant material may be therapeutic, medicinal, for consumption (as a food ingredient), etc. Examples include chemical materials that are endogenous to the solid plant material and that may be considered to be hydrophobic or lipophilic, such as essential oils, plant lipids, plant lipid oils, plant waxes, plant resins, chlorophylls, cannabinoids, fatty acids, terpenes, terpinoids, oil soluble vitamins, other aromatic compounds, flavonoids, and lactones.

Example target plant materials may typically be plant materials that are considered to be lipophilic, and that are endogenous to a plant and solid plant material, i.e., originally present in the plant.

In some embodiments, the target plant material is a "plant essential oil." Essential oils are hydrophobic oils derived from material of a plant, that are initially contained in the plant and not added, i.e., not exogenous. Essential oils may be made mostly or entirely of terpenes or terpenoids, and may include other chemical constituents such as alcohols, aldehydes, esters, propionates, butyrates, valerates, capropates, and phenols. Essential oils may impart a composition that contains the essential oil with certain particular flavors or odor that are characteristic of the type of essential oil. Plant essential oils can be obtained from plant parts such as rinds/peels, leaves, flowers, buds, rhizomes, bark, resins, seeds, berries, roots, and fruits.

Some essential oils are obtained from citrus fruits. For example, using methods and systems of the disclosure citrus essential oils can be obtained from fruits such as orange (e.g., from orange rinds), lemon, lime, grapefruit, pomelo, mandarin, tangerine, and clementine, etc. Other essential oils can be obtained from other plant types such as allspice, juniper, cumin, cinnamon bark, camphor, rosewood, ginger, basil, eucalyptus, lemongrass, peppermint, rosemary, spearmint, chamomile, clove, jasmine, lavender, and rose, and clove oil. A plant essential oil obtained from the system and method of the disclosure can be used for therapeutic, nutritional, cosmetic, food, and flavor and fragrance purposes as discussed herein.

In some examples, method and compositions of the present description are used to obtain essential oils from hops. The main components of hops essential oils are terpene hydrocarbons that are of myrcene, humulene, and caryophyllene. These particular terpenes can represent about 80 to 90 percent of the essential oils in hops. Myrcene can impart the smell of fresh hops while humulene can impart a distinctive hop aroma.

Terpenes are well known chemical compounds commonly found in essential oils and natural resins. Terpenes are generally known to have a pleasant aromatic odor, to be present in coniferous plants, and also in many essential oils. Chemically, terpenes are considered to include any of various isomers of unsaturated $C_{10}H_{16}$ hydrocarbon molecules or their functionalized derivatives (i.e., terpenoids) found in essential oils and oleoresins of plants such as conifers and used in organic syntheses. Terpenes that are modified chemically, such as by oxidation or rearrangement of the carbon skeleton are referred to generally as "terpenoids." Terpenes and terpenoids, including cannabinoids, are generally non-polar substances and hence soluble in lipids, i.e., hydrophobic or lipophilic.

Exemplary terpenes include, but are not limited to pinene, limonene, terpinene, terpinen-4-ol, carvacrol, carvone, 1,8-cineole, p-cymene, fenchone, β-myrcene, cannaflavin A, cannaflavin B, nerolidol, phytol, and squalene. Exemplary terpenoids include, but are not limited to, cannabinoids, limonene oxide, pulegone-1,2 epoxide, salviorin A, hyperforin, and pyrethrins.

According to certain described examples, plant extract compositions, compositions, systems and methods of the present disclosure involve target plant materials in the form of oils from cannabis or hemp. Cannabis produces over 60 cannabinoids, including tetrahydrocannabinol (Δ9-THC), the main psychoactive constituent of cannabis, as well as cannabidiol (CBD), which is not psychoactive but has many potential medical applications.

According to useful examples, the system, methods, and plant extract compositions of the present disclosure are used to extract one or more target plant materials that are cannabinoids, from solid plant material. Exemplary cannabinoids include, but are not limited to, cannabinol (CBN), cannabinolic acid (CBNA), A(9)-tetrahydrocannabinol (A(9)-THC), Δ(9)-tetrahydrocannabinolic acid (A(9)-THCA), A(9)-cannabidiol (A(9)-CBD), Δ(9)-tetrahydrocannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-tetrahydrocannabidiol (Δ(8)-CBD), Δ(8)-tetrahydrocannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA), Cannabidivarin (CBDV) and Tetrahydrocannabivarin (THCV).

Other terpenes that are different from cannabinoids that can be obtained from hemp and cannabis include terpineol, limonene, myrcene, terpinolene, humulene and sesquiterpenes. These non-cannabinoid terpenes, can impart aroma characteristic of cannabis. Combinations of different cannabinoids, or cannabinoids and non-cannabinoid terpenes can provide synergetic interaction, and the methods of the disclosure can provide compositions with combinations of these different terpenes, or the terpenes can be refined to provide purified terpene components.

Lipids are compounds that are based on fatty acids and derivatives of fatty acids. Lipid oils are defined as oils that are based on fatty acids and derivatives of fatty acids (such as glyceride oils), whereas many essential oils have a base of terpene hydrocarbons. The term "fatty acid" includes for example short-chain and long-chain saturated and unsaturated (e.g., monounsaturated and polyunsaturated) hydrocarbons comprising one carboxylic acid group. Derivatives of fatty acids include fatty acid esters, glycerides, phosphoesters, etc. In embodiments, a system, method, or composition of the disclosure are used to extract one or more cannabinoid from a plant.

The term "waxes" as used in this disclosure shall be taken to mean naturally occurring species in the essential oil that are able to impart cloudiness to the oil product at temperatures below 20° C. Typical wax compounds that may be derived from plant material, often present in essential oils, include long-chain aliphatic hydrocarbons (typically C14 or longer), long-chain alcohols (typically C14 or longer), related ketones, aldehydes, acids, diols, etc., and coumarins, sterols, flavonoids.

According to the present description and extraction processes, an extraction medium can be contacted with solid plant material in an extraction step as described, with endogenous target plant material being removed from the solid plant material to become dissolved, suspended, or otherwise contained in the liquid extraction medium. An oil phase of the resultant liquid extraction medium that contains the target plant material, as well as derivatives of that oil phase, is sometimes referred to herein as a "plant extraction solution."

A plant extract composition can be in a form of a single phase solution alone, i.e., with no other phases, or may optionally be included as one phase of a larger composition that includes multiple phases, e.g., an emulsion. For example, a composition that contains the plant extract composition as a first liquid phase may contain the plant extract composition as a continuous or a discontinuous phase along with a second liquid phase, which may be discontinuous or continuous, respectively. In other examples, a composition that contains the plant extract composition as a first phase may contain the plant extract composition as a continuous liquid phase along with a second phase that is solid, e.g., particles. Before subsequent processing of the plant extract composition (e.g., downstream processing to separate the surfactant and target plant material from the plant extract composition) that is part of a multi-phase composition, a useful or preferred method may include a process of separating any additional solid or liquid phase from the plant extract composition, and the plant extract composition can be further processed as substantially a single (non-aqueous, oil) phase.

The amount of target plant material in a plant extract composition may be any useful amount consistent with the present description, for example an amount that will be useful and efficient as part of a plant extract composition used in a chemical extraction process to separate desired target plant material from solid plant material. Useful and preferred amounts will also allow for efficient downstream processing of the plant extract composition to separate the target plant material from the plant extract composition to produce a concentrated liquid, solid, or gaseous form of the target plant material, sometimes referred to generally as a "concentrated plant extract."

Examples of amounts of total plant material (target plant material as well as non-target plant material) in a plant extract composition can be at least 1, 2, or 5 weight percent (based on total weight of the plant extract composition), and may be up to or in excess of 10, 20, 30, 40, 50, 60, 70, 80 weight percent lipophilic plant material based on total weight of the plant extract composition.

Examples of amounts of target plant material in a plant extract composition, or a derivative thereof produced by further processing, may be at least 1, 2, or 5 weight percent (based on total weight of the plant extract composition), and may be up to or in excess of 10, 20, 30, 40, 50, 60, 70, 80 weight percent lipophilic plant material based on total weight of the plant extract composition. Concentrations of the target plant material in a plant extract composition that are in the middle or higher end of these ranges may be preferred, such as a concentration in a range from 10 to 55 weight percent, e.g., from 20, 25, or 30 up to about 50 weight percent target plant material in the plant extract composition.

The target plant material can include a specific desired compound or group of compounds that are specifically desired to be extracted from the solid plant material and formed into a concentrated plant extract. At different stages of an extraction process, the plant extract composition will typically contain a mixture of one or more target plant materials (target compounds) with non-target plant materials (which may also be lipophilic) that are different from the target compound, e.g., non-target lipophilic plant material.

According to certain process examples, during or after different stages of processing (e.g., during a chemical extraction process or during downstream processing), the amount of the target plant material as a portion of the total amount of endogenous plant material that is contained in a plant extract composition can be relatively high, e.g., at least 30, 40, or 50 weight percent, preferably at least or in excess of 60, 70, 80, 90, or 95 weight percent, based the total weight of all endogenous plant materials in the plant extract composition.

In other embodiments, such as for isolating and collecting target compounds (terpenoids, cannabinoids, etc.) that have a very high monetary value (by mass), due to a specialized use, or that are present endogenously in a low amount in a plant material, the amount of the target plant material as a portion of the total amount of endogenous plant material that is contained in a plant extract composition may be lower, e.g., below 20, 10, 5, or even 1 percent by weight, based on total weigh plant extract composition.

A non-target plant material is any plant material that is different from a target plant material. Examples (depending on the target compound and the type of solid plant material) may include one or more of a lipophilic plant material selected from: plant essential oils, plant lipids, plant lipid oils, plant waxes, plant resins, chlorophylls, cannabinoids, fatty acids, terpenes, terpinoids, oil soluble vitamins, other aromatic compounds, flavonoids, and lactones. According to example processes and plant extract compositions, examples of non-target plant materials may alternately be target materials.

For a plant extract composition that includes cannabinoids as a target plant material (a.k.a. "target compound"), example non-target plant materials, e.g., example non-cannabinoid lipophilic plant materials include: plant essential oils, plant lipids, plant lipid oils, plant waxes, plant resins, chlorophylls, fatty acids, terpenes, terpinoids, oil soluble vitamins, other non-cannabinoid aromatic compounds, flavonoids, and lactones.

Certain specific example plant extract compositions (e.g., at different stages of processing such as during a chemical extraction process or during downstream processing) can contain at least 1, 3, 5, 10, or 15 weight percent surfactant, and least 1, 3, or 5 weight percent endogenous plant material that is endogenous to the original solid plant material (i.e., derived from the solid plant material), and that is dissolved, suspended, or otherwise contained in the composition, based on total weight plant extract composition. The endogenous plant material may be a combination of target plant material and non-target plant material. In specific examples, the plant material contained in a plant extract composition may be a combination of cannabinoids and non-cannabinoid plant materials. For example, a plant extract composition that includes cannabinoids as a target compound may contain at least 15 weight percent surfactant, at least 5 weight percent cannabinoid derived from plant material and dissolved in the solution, and at least 1 weight percent non-cannabinoid lipophilic plant material dissolved in the surfactant and derived from the plant material, based on total weight plant extract composition.

With added detail, at any of the different stages of processing, specific example plant extract compositions can contain from 15 to 30, up to or in excess of 40, 50, 60, 70, or 80 weight percent surfactant, and at least 13, or 5, up to or greater than 10, 20, 30, 40, or 50 weight percent endogenous plant material derived from plant material and contained (e.g., suspended, dissolved, or emulsified) in the plant extract composition, based on total weight plant extract composition.

Example plant extract compositions that include cannabinoids as a target plant material may contain from 15 up to or in excess of 30, 40, 50, 60, 70, or 80 weight percent surfactant, and at least 5, up to or greater than 10, 20, 30, 40, or 50 weight cannabinoid derived from plant material and contained in the plant extract composition, and from 1 to 20, e.g., from 2 to 10 or 15 weight percent non-cannabinoid plant material contained in the plant extract composition and derived from the plant material, based on total weight plant extract composition.

According to certain specific examples of methods useful to extract cannabinoids, a plant extract composition may contain up to or in excess of 1, 5, 10, 20, 30, 40, 50, 60, 70, 80 weight percent of a target plant material (e.g., cannabinoids), and an amount of from 1 to 20, e.g., from 1 to 5, 10, or 15 weight percent non-target plant material (e.g., non-cannabinoid lipophilic plant material). The balance or a large portion thereof may be surfactant of a type referred to herein as a high KB surfactant, or tertiary amide surfactant, pH-dependent surfactant, detergent-type surfactant, or a combination of these; e.g., the plant extract composition may contain from 10, 20, 30, or 40, up to or in excess of 50, 60, 70, 80, or 90 weight percent high KB surfactant or tertiary amide surfactant, pH-dependent surfactant, detergent-type surfactant, or a combination of these, based on total weight of the plant extract composition. The plant extract composition may contain not more than a small amount of other processing liquids, endogenous oil, or endogenous organic solvent, e.g., not more than 5, 1, 0.5, 0.1, or 0.05 weight percent total endogenous oil, and endogenous organic solvent, based on total weight of the plant extract composition.

A plant extract composition can be prepared by any method that combines the ingredients of the surfactant (any type, but particularly an amide surfactant, a high KB surfactant, amide-based surfactant, pH-dependent surfactant, detergent-type surfactant, or a combination of these) with an amount of target plant material. Useful methods involve mechanical processing of solid plant material followed by or in combination with one or more chemical extractions steps that cause desired target plant material to become dissolved in or otherwise contained in a liquid extraction medium that contains one or more surfactants as described, other optional processing ingredients such as acid, base, chelating agent, hydrotrope, solubilizing agent, etc., and optionally not more than a low or insubstantial amount of exogenous oil, exogenous organic solvent, or both.

As a more specific example, useful methods for extracting lipophilic plant material from solid plant material may include steps of a) obtaining solid plant material that contains a desired target plant material; b) mechanically processing the solid plant material before or during a process of contacting the solid plant material with a liquid extraction medium as described, wherein the liquid extraction medium: has a basic pH, contains at least one pH-sensitive surfactant that causes the liquid extraction medium to form an emulsion, and contains at least one high KB or amide surfactant that contains dissolved target plant material; c) lowering the pH of the liquid extraction medium, wherein the lowered pH facilitates de-emulsification of the liquid extraction medium and separation of the emulsion to produce of an oil phase that contains at least one high KB or amide surfactant that contains dissolved target plant material; where, at the lowered pH conditions, the pH-sensitive surfactant: i) partially or fully loses its ability to form an emulsion that contains endogenous lipophilic and hydrophilic materials of the processed plant material, ii) partially or fully disassociates with the target plant material, iii) is chemically cleaved into two or more surfactant by-products, or any combination of i)-iii); and d) separating oil phase from the de-emulsified liquid extraction medium. The oil phase may be further processed to isolate, collect, and optionally purify the target plant material.

This type of example method can optionally or preferably include one or more additional method steps such as: supplying one or more endogenous process materials selected from: water, steam, organic solvent, oil, chemical additives such as surfactants, acids, base, chelating agent, anti-corrosion agent, hydrotrope, solubilizer, anti-solvent, etc., from supply sources to one or more parts the system; forming an aqueous composition that includes the surfactant and base; processing the solid plant material; moving the solid plant material; applying shear, mixing, pressure, or two more of these; mechanically grinding or otherwise reducing a size of the plant material in the aqueous composition or extraction medium; separating fiber from the processed plant material; removing fiber from plant material; changing the temperature of extraction medium; filtering processed plant material/aqueous composition; back-flushing parts of the system; changing pH of the aqueous composition or extraction medium using an acid or by electrolysis; blending chemicals; electrolyzing the aqueous composition or extraction medium; removing acidified aqueous composition; changing pH of the aqueous composition or extraction medium using base or electrolysis; centrifuging the aqueous composition or extraction medium; recycling the regenerated, restored, and adjusted surfactant back into the process cycle; separating the target plant material from the extraction medium; storing the target plant material; treating or regenerating the surfactant, such as with a base material or by cathodic treatment; treating with a metal chloride such as iron chloride; precipitating chlorophyll, such as iron-chlorophyll; providing a preparation of iron-chlorophyll, among other optional steps or processes.

In another aspect, the disclosure provides a system for extracting target plant material from solid plant material. The system can be used to carry out a method of the present disclosure. The system may include an apparatus that mechanically processes plant material in an aqueous composition (e.g., liquid extraction medium) that includes surfactant (as described herein), an optional pH-lowering feature (e.g., a base) that lowers that pH of the aqueous composition, optional chemicals that improve separation of target materials from processing chemicals (surfactants, hydrotropes, solubilizers, antisolvents, additives) and non-target materials, and a separator, separating equipment, or separation steps useful for separating the surfactant from the target plant material, e.g., separating the target plant material from the aqueous composition (e.g., liquid extraction medium).

The system can optionally or preferably include one or more additional system features such as supply containers (such as for water, solvents, chemicals, such as surfactants, acids, base), etc.), tanks (e.g., storage tanks, mixing tanks, etc.), plant supply bins or containers, conveyors, hoppers, pump, valves, motors, filters (e.g., screens, large pore filters, small pore filters, resins), blenders and agitators, electrolysis equipment (e.g., anodes, cathodes, power supplies), steam producing equipment including steam injectors, centrifuges, pumps, fluid conduits for moving liquid compositions from one part of the system to another, waste containers, safety features including stops and cut-off apparatus, electronic sensors and control apparatus, such as process control system(s) (e.g., a computer), for monitoring and controlling system features such as pumps, valves, electrocells, blenders, and motors, including auger (expeller, feed), and macerator.

The system and method of the disclosure can be used to process any solid plant material that includes a desired target plant material, such as target plant materials that are lipophilic. In embodiments, the system and method of the disclosure are used to process entire cannabis, echinacea, or hemp, or any portion thereof, as the solid plant material. The cannabis, echinacea or hemp can be selected from those that are naturally occurring, hybrids, and genetically engineered versions of these plants. Exemplary species of the Cannabis genus include, but are not limited to *C. indica, C. sativa*, and *C. ruderalis*. Exemplary species of the *Echinacea* genus, include, but are not limited to *E. pallida, E. angustifolia, E. purpurea*.

Genetically modified cannabis plants, such as those that have modified expression of tetrahydrocannabinolic acid (THCA) synthase, and modified amount of delta-9-tetrahydrocannabinol (THC), cannabidiol (CBDA), and cannabidiol (CBD), are known from references such as WO2016189384A1.

Hops, or *Humulus*, is a genus of the Cannabinaceae family, and include species such as *Humulus lupulus*. Exemplary species of the *Chrysanthemum, Argyranthemum, Leucanthemopsis, Leucanthemum, Rhodanthemum*, and *Tanacetum* include *Tanacetum cinerariifolium* and *Chrysanthemum coccineum.*

Other types of plants that can be processed as the solid plant material include plants that produce any type of biomass, such as wood-producing plants, bygasse-producing plants, such as sugar cane, as well as any other plants that are used for food products and that parts that are disposed of (e.g., citrus rinds, etc.).

A system or method of the disclosure can use the whole plant or any part, or combination of parts thereof as solid plant material. For example, the plant parts can be selected from buds, leaves, flowers, stems, stalks, roots, and seeds, and any combination thereof.

The methods and systems of the disclosure can be used to process parts of plants that have trichomes, which are epidermal outgrowths covering aerial plant tissues. Trichomes can be glandular or nonglandular, with glandular trichomes characterized by metabolite secreting or storing cells. Glandular trichomes can make, store, and/or secrete metabolites such as terpenoids. (see, for example, Huchelmann, et al. (2017) Plant Glandular Trichomes: Natural Cell Factories of High Biotechnological Interest, Plant Physiol. 175:6-22).

Optionally, the plant or plant part can be treated with one or more enzymes to promote processing of the plant and release of a desired (e.g., lipophilic) target plant material. Exemplary enzymes that can be used to treat plant material including cellulases, beta-glucosidases, hemicellulases, xylanases, glucanases, beta-glucanases, pectinases, amylases, alpha-amylases, phospholipases, beta-mannanases, arabinanases, phytases, and proteases.

Enzymes such as pectinases and/or cellulases can be used to treat solid plant materials that have trichomes, such as to enhance release of terpenes from these structures. The solid plant material can be treated with enzymes for a period of hours or days prior to introducing the solid plant material into the system for extraction and purification of target plant material.

The disclosure provides systems and methods for the extraction of lipophilic plant materials from a plant or portion thereof. An exemplary system for extraction is described with reference to FIG. 1.

Extraction system 10 can include a container 12 that holds solid plant material in the form of plants, plant parts, plant pieces, or particles of plants, or the like, that is to be subjected to the extraction process. The container can hold solid plant material that is fresh (i.e., recently harvested) or that is partially or fully dehydrated. The amount of water present in the solid plant material (e.g., as a percentage of plant solids) can be determined and the processing parameters can be adjusted accordingly to optimize the extraction process. For example, plants that are substantially or fully dehydrated may be mixed with surfactant composition or liquid extraction medium having a higher amount of water, whereas plants that are fresh (substantially or fully hydrated) can be mixed with a concentrated surfactant composition, or with a liquid extraction medium, having a lower amount of water. While the terms "surfactant composition" and "liquid extraction medium" may or may not have precisely the same meaning, where the term "surfactant composition" is used in the present descriptions, it is understood that the term "surfactant composition" could be replaced by the term "liquid extraction medium."

In example methods, the ratio of surfactant (all types) to water can be constant for a starting concentration of oil (target material, such as CBD) in the plant (on a dry basis).

In these or other example methods, the ratio of liquid extraction medium to dry plant material that are combined, by weight, can be from about 1:1, to about 10:1 (liquid extraction medium:plant material). On a basis of liquid extraction medium (plus water present in the plant material) to plant material (on a dry basis), a useful or preferred range may be from about 6:1 to 2:1, e.g., from about 5:1 to about 3:1, or a ratio of about 4:1 (liquid extraction medium (plus water present in the plant material):plant material (on a dry basis)).

Alternately or in addition, example methods may be performed by combining an amount of liquid extraction medium with plant material in relative amounts of surfactant (all types, or a single type such as high KB surfactant) in the liquid extraction medium, relative to lipophilic plant material (in a solid plant material), being at a ratio of from 0.1 to 99 grams surfactant per 1 gram lipophilic plant material, e.g., from about 1 or 1.5 to about 10, 20, 50, or 70 grams surfactant per 1 gram lipophilic plant material, e.g., from bout from 0.3 to 3 or 5 grams surfactant per 1 gram lipophilic plant material (total target plant material plus non-target plant material) (in a solid plant material), e.g., from 1 to 2 grams surfactant (all types, in a liquid extraction medium) per gram target lipophilic plant material (in the solid plant material), or from 1.2 to 1.5 grams surfactant (all types, in a liquid extraction medium) per gram target lipophilic plant material (in the solid plant material).

Alternately or in addition, example methods may be performed by combining an amount of liquid extraction medium with plant material in relative amounts of amide-based or high KB surfactant in the liquid extraction medium, relative to lipophilic plant material (in a solid plant material), being at a ratio of about 1 gram amide-based or high KB surfactant per 1 gram lipophilic plant material (total target plant material plus non-target plant material) (in a solid plant material), e.g., from 0.8 to 1.2 gram amide or high KB surfactant (in a liquid extraction medium) per gram target lipophilic plant material (in the solid plant material).

Alternately or in addition, the surfactant composition or liquid extraction medium may be heated, e.g., to a temperature that is effective to form a stable emulsion, for example to a temperature in a range from ambient temperature to about 100 degrees Celsius, such as from 30 degrees Celsius to about 70 degrees Celsius.

Referring again to FIG. 1, example extraction system 10 includes conveyor 14 that moves the solid plant material to hopper 16, which feeds the plant materials (also referred to as "plant or plant parts") into mechanical processor 18, such as an auger, that causes release of plant materials (including target plant materials and non-target plant materials) from the plants by application of pressure. Release of the target and non-target plant materials by one or more mechanical actions on the plant or plant parts occurs in the presence of surfactant (of a type or types and amounts described herein), which is supplied from a surfactant composition or liquid extraction composition. The surfactant composition is an example of a "liquid extraction medium."

The surfactant composition or liquid extraction composition is preferably at a basic pH, and is preferably in the form of an emulsion, when brought into contact with the solid plant material. Adding the surfactant composition or liquid extraction medium to the solid plant material can form an aqueous, surfactant-and plant material-containing plant composition. The mechanical processor 18 will be described in more detail herein.

Extraction system 10 can include a plant compressor (not shown) between hopper 16 and mechanical processor 18. The plant compressor can be a compression auger that increases the pressure of the solid plant material being processed before the solid plant material is fed into the mechanical processor, which, in embodiments, can be an "expeller auger." Embodiments of the system can use a compression auger-expeller auger combination.

Extraction system 10 can also include a slurry tank (not shown) which aids in feeding a mixture of solid plant material and surfactant composition into the auger. The slurry tank can include a feature such as a paddle that can agitate the mixture as it is fed into the auger system. The slurry tank can also include one or more enzymes that can facilitate digestion of the solid plant material and release of the target and non-target plant materials, e.g., lipophilic plant materials. The mixture also contains the surfactant composition (or liquid extraction medium) that contains surfactant and base, and if an enzyme is used in the mixture these components are preferably compatible.

The mixture can be moved from the slurry tank into the compression auger, which includes a positive pressure pump that pressurizes the auger up to at least 150 psi (gauge), or greater, thereby facilitating throughput and extraction efficiency. The compression augur will compress (pressurize) the solid plant material to a pressure that is at least or in excess of 50, 100, 200, 400, 600, 800, or 1000 pounds per square inch (gauge), or higher. Advantageously, these pressures produce a relatively dry stream of processed plant material that does not contain a substantial amount of moisture.

According to useful or example methods of mechanical separation, a two-stage auger with high pressure may be effective or advantageous for extracting a target plant material (any type, for example cannabinoid, terpene (including terpenoids), CBDA, or the like) from a solid plant material (e.g., hemp, or another). A two-stage auger allows for a step of washing and pressurizing (squeezing) the plant extract a first time, and then a second time. The first washing and pressurizing step occurs in the first stage of the auger and the second washing and pressurizing step occurs in the second auger stage. During the first and second stages, pressure applied to the plant extract material increases when the material moves from the inlet, through the first stage, then through the second stage, to the outlet. Example or representative pressures measured within the auger cylinder may be below 500 psi (gauge) at the inlet, e.g., in a range from 200 to 400 psig at the inlet; in a range from 300 to 800 psig in the first stage and also in the second stage, with a pressure in the second stage being greater than pressures in the first stage; and a pressure of at least 700, 800, 900, or even 1000 psig at the outlet. This mechanical processing using a high pressure two-stage auger allows highly efficient removal of liquid materials, including target plant material, from plant material. In example methods, at least 90, 95, 98, or 99 percent of endogenous liquids may be removed from plant material entering the two-stage auger. Processed plant material leaving the outlet of the two-stage auger may contain less than 10, 5, 2, or 1 percent.

Extraction system 10 can also include a macerator (not shown) which can grind the plant or portions thereof into smaller particles with can be fed into the auger, or into the slurry tank. Preferred particle sizes are less than 1 inch, or less than ½ inch, such as particles in the range of about 1/32 inch to about ½ inch.

The mechanical processor 18 can be in fluid communication with a surfactant composition supply tank 22, which can supply a desired amount of surfactant-containing composition (e.g., "surfactant composition" or "liquid extraction medium") to mechanical processor 18 via conduit 24. The supply tank 22 can be in fluid communication with a water source/conduit (not shown), a surfactant source 26/conduit 28, and a basic chemical source 30/conduit 32. If more than one surfactant is used, the system can include one more additional surfactant sources/conduits. Water, surfactant, and a basic chemical can be metered into the tank 22 and mixed together to provide an aqueous composition with a desired concentration of surfactant at a desired pH. The concentration of the surfactant in the supply tank 22 can vary greatly (e.g., from dilute to concentrated compositions) and can be formulated based on one or more processing features such as the plant type and amount of water in the plant immediately prior to processing.

Optionally, the amount of surfactant used in methods of the disclosure can be expressed with reference to the amount of surfactant solids when the surfactant composition is mixed with the plant material, for example in the mechanical processor 18. The mixture can includes one or more surfactants and endogenous solid and liquid materials of from the plant, and optionally any base and water from the aqueous surfactant composition having a basic pH. When combined with the plant material, the mixture can have a total amount of one or more surfactants in the range of about 0.1% (wt) to about 25%, 30%, or 50% (wt), e.g., from about 0.25% (wt) to about 20% (wt), about 0.5% (wt) to about 15% (wt), about 1% (wt) to about 10% (wt), about 1.5% (wt) to about 7.5% (wt), or 2% (wt) to about 5% (wt).

The liquid component in the surfactant composition that is not surfactant is preferably water. For example, the liquid component in the surfactant composition (that is not surfactant) may be greater than 50% (vol) water, about 60% (vol) or greater water, about 70% (vol) or greater water, about 80% (vol) or greater water, about 90% (vol) or greater water, about 95% (vol) or greater water, about 97% (vol) or greater water, about 98% (vol) or greater water, about 99% (vol) or greater water, or about 99.5% (vol) or greater water, or the liquid component consists essentially of water.

In some modes of practice, a water-immiscible organic solvent (or "water-immiscible solvent") may be added to the surfactant composition. A water-immiscible solvent may be effective to facilitate separation of lipophilic plant materials from surfactant; e.g., after a surfactant composition or a liquid extraction medium (either one being in a form of an emulsion) is processed to a reduced pH to disrupt the emulsion and form an aqueous phase and a non-aqueous phase (oil phase), the non-aqueous phase will contain surfactant and lipophilic plant material. Water-immiscible solvents such as hexane, pentane, or propyl bromide, silicon-based oils, fluorinated solvents, mineral oils, and terpentines, as part of the non-aqueous phase can facilitate separation of the surfactants from the non-aqueous phase, and these solvent compounds can be easily separated from cannabinoids or other target plant material at a later stage in processing, such as by refining.

In modes of practice, the aqueous surfactant composition uses no or very little exogenously added organic solvent(s)/liquid(s). For example, the system and methods of the disclosure do not require the introduction of any substantial amount of "exogenously" added organic solvent (e.g., ethanol, petroleum oils, vegetable oils) in order to obtain useful or high yields of lipophilic plant material. Preferably, if any solvent is present, it is in an amount of less than 5% (wt), less than 2.5% (wt), less than 1% (wt), less than 0.5% (wt), less than 0.1%, or less than 0.01% (wt). However, it is understood that some oils that are naturally-occurring are released from the plant during processing, but such oils are "endogenous" which are not "exogenously added" ("exogenous") as discussed herein.

The pH of the surfactant composition (e.g., liquid extraction medium) can be adjusted with one or more bases, which can be supplied from the basic chemical source 30/conduit 32, and mixed with surfactants in supply tank 22. Exemplary bases include inorganic and organic bases. Examples of inorganic bases are alkali metal or alkaline earth metal hydroxides such as potassium hydroxide, sodium hydroxide, lithium hydroxide, and calcium hydroxide; alkali metal or alkaline earth metal carbonates such as calcium carbonate, sodium carbonate, sodium hydrogencarbonate, and lithium carbonate; alkali metal or alkaline earth metal phosphates such as sodium phosphate; alkali metal or alkaline earth metal oxalates such as sodium oxalate; alkali metal or alkaline earth metal acetates such as sodium acetate; and basic oxides such as calcium oxide and aluminum oxide. Examples of organic bases include, but are not limited to, tetramethylammonium hydroxide, ammonia, ammonia hydroxide, diethylamine, trimethylamine, triethylamine, ethanolamine, pyridine, triethanolamine, imidazole, and ethylenediamine.

When the surfactant composition or liquid extraction medium is applied to solid plant material, e.g., as surfactant composition or liquid extraction medium is contained in tank 22, the surfactant composition or liquid extraction medium has a pH that may be effective to form an emulsion, and to maintain the emulsion upon contacting the solid plant material. When the surfactant composition or liquid extraction medium is applied to and combined with the solid plant material, chemical materials that are present as part of the solid plant material may have a pH-reducing effect, e.g., may reduce the pH of the surfactant composition or liquid extraction medium. For this reason, the surfactant composition or liquid extraction medium is brought to a relatively higher pH before the surfactant composition or liquid extraction medium is applied to the solid plant material. An example of a pH of a surfactant composition or liquid extraction medium before the surfactant composition or liquid extraction medium is contacted with solid plant material may be above 10, e.g., in a range from 10.5 to about 11.5, e.g., from about 10.7 to about 11, depending on the amount of reduction in pH that the surfactant composition or liquid extraction medium will experience when combined with the solid plant material, which in turn depends on the chemical makeup of the solid plant material.

Referring back to FIG. 1, the processor 18 includes one or more features that allow the plant material to be subjected to one or more mechanical treatments, such as pressing, crushing, grinding, macerating, cutting, chopping, blending, pureeing, or a combination thereof. Alternatively, or in combination with another mechanical processor, the system can use a sonicator to cause release of lipophilic plant material from the plant or portion thereof. A sonicator is an apparatus that can generate ultrasonic waves (sound energy) to facilitate extraction of the lipophilic plant material.

In a preferred aspect, the processor is a mechanical processor than presses the plant or portion thereof. In one embodiment, the mechanical processor 18 can include a housing 34 that contains an auger 36. A motor 38 can be attached to and causes rotation of the auger 36 in the housing, and can apply pressure to the plant or portion thereof to cause release of the lipophilic plant material in the presence of the surfactant composition.

Figure 2A:
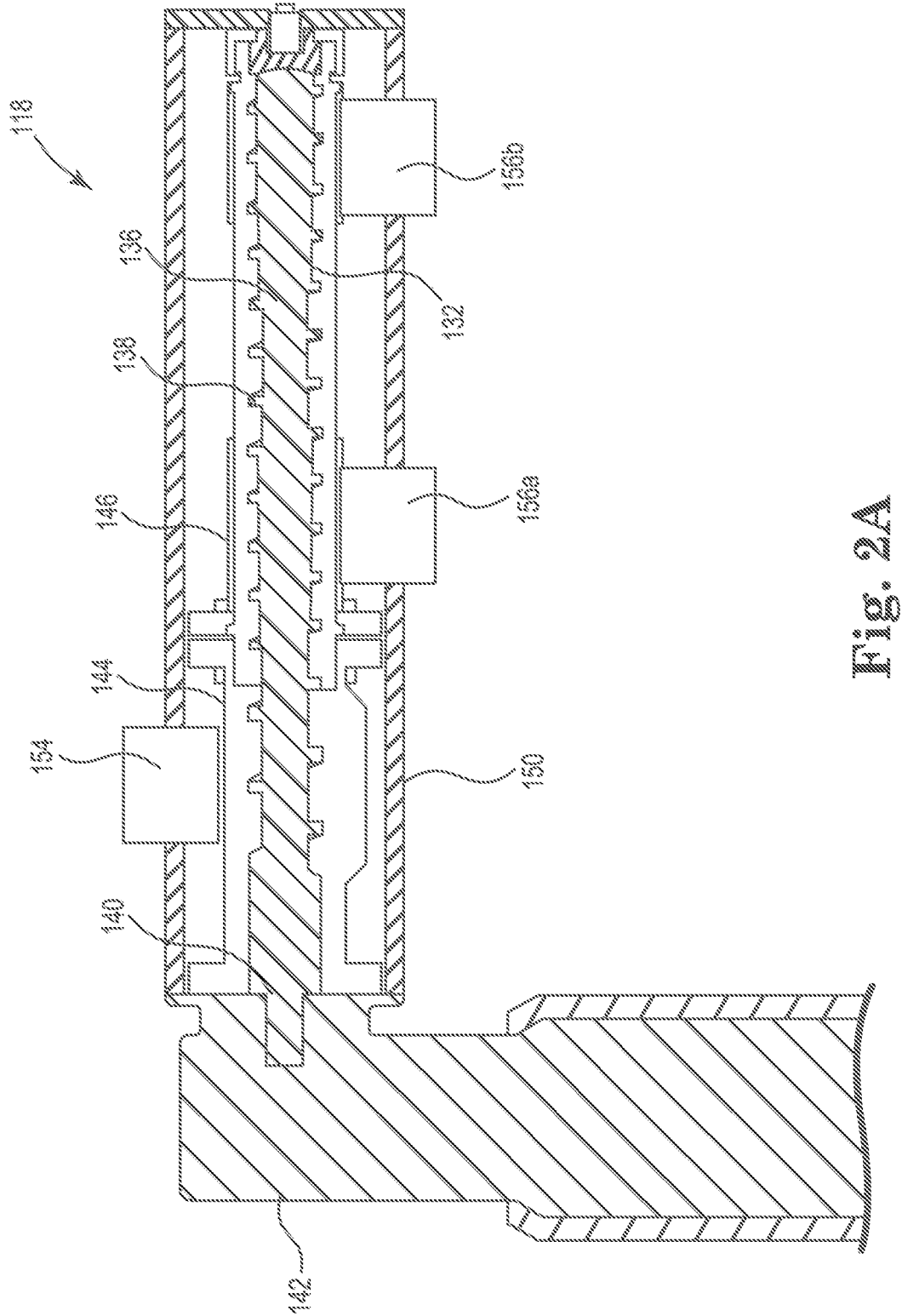
FIG. 2a is a cross-sectional view of a mechanical processor including an auger for processing plants, according to an embodiment of the disclosure.

FIG. 2A shows a more detailed view of an embodiment of the mechanical processor. In particular, FIG. 2A shows a cross-section of a mechanical processor 118 with an auger 132. The processor 118 includes an auger 132 with an auger shaft 136 and auger blades 138 arranged helically around the shaft 136, and a proximal end 140 that engages a rotational member of motor in a motor housing 142. The auger is movable within an elongated hollow internal assembly, which includes a proximal internal portion 144 and distal internal portion 146. The auger 132, proximal internal portion 144, and distal internal portion 146, are within an auger housing 150. The auger housing can include a plant inlet port 154 through which plant portions are introduced into the auger. The auger housing can also include a surfactant composition inlet port (not shown) through which the surfactant composition is introduced into the auger. The auger housing can also include one or more outlet ports) (156a, 156b) through which the composition that includes the lipophilic plant material and surfactant (e.g., the liquid extraction medium, now containing lipophilic plant material) from the processed plant is removed from the mechanical processor. The auger housing can also include an outlet port (not shown) through which waste plant material, such as plant fiber, is removed from the mechanical processor. For example, plant fiber can be moved out of the nose (distal end) of the auger and pumped by a positive pressure pump to a waste container. Further, the method of the disclosure can also include recycling at least a portion of previously extracted plant material to improve yield of the target (e.g., lipophilic) plant material.

Figure 2B:
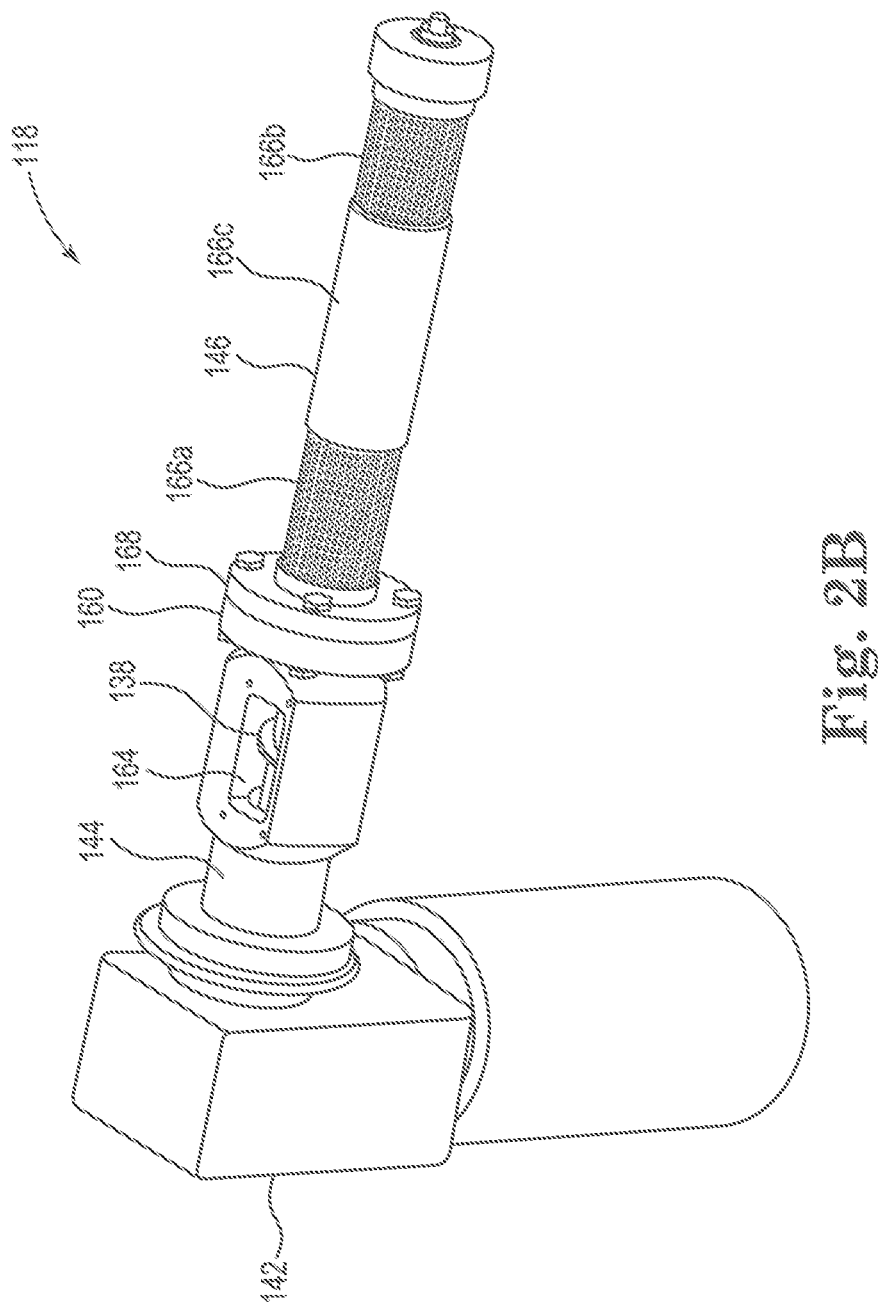
FIG. 2b is a perspective view of a mechanical processor including an auger for processing plants, according to an embodiment of the disclosure.

FIG. 2B is a perspective view of the mechanical processor shown in FIG. 2A. The auger blade 138 is shown through an opening 164 in the proximal internal portion 144. Plant parts can be introduced through opening 164 and into the proximal internal portion 144, for processing by the auger. Rotation of the auger within the proximal and distal internal portions (144, 146) causes pressure to be applied to the plant or portion thereof and release of the lipophilic plant material into the surfactant composition. By rotation of the auger, processed plant material and surfactant composition with lipophilic plant material is moved in a proximal to distal direction in the proximal and distal internal portions (144, 146). The proximal and distal internal portions (144, 146) can be connected together at flange portions 160 and 168. The distal internal portion 146 includes sections 166a and 166b which have openings through which the surfactant composition with lipophilic plant material can flow through. The distal internal portion 146 can also include section 166c between sections 166a and 166b which does not include apertures. Referring back to FIG. 2A, after the surfactant composition with lipophilic plant material flows through the openings in sections 166a and 166b, it can be removed from the mechanical processor through one or more outlet ports (156a, 156b).

Figure 3:
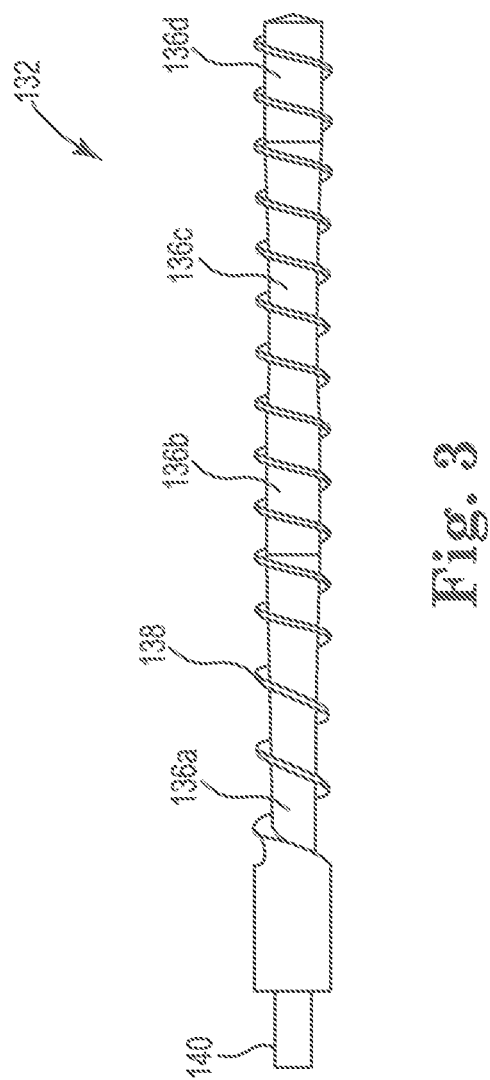
FIG. 3 is a perspective view of auger of a mechanical processor, according to an embodiment of the disclosure.

FIG. 3 is an illustration of the auger shaft 136 and auger blades 138 arranged helically around the shaft 136, and a proximal end 140 that engages a rotational member of motor in a motor housing 142. The auger 136 has proximal end 140 that engages a rotational member of motor in a motor housing 142. The embodiment shown in FIG. 3 has an auger shaft 136 that varies in diameter from its proximal to distal end. For example at points 136a and 136c, the auger shaft has a smaller diameter than at points 136b and 136d. However, the diameter of the auger blades can be the same or approximately the same along its length. Therefore, the height of the blades can be greater at points 136a and 136c than the height of the blades at points 136b and 136d.

The system can be operated at one or more temperatures in a broad temperature range, such as at temperatures in the range of about −86° C. to about 300° C. In some modes of practice, an optimum temperature can be chosen for a particular extraction fluid recipe to extract a particular target compound that will give the least contamination from other compounds. Different parts of the system can be operated at different temperatures. In some modes of practice, parts of, or all of the system is operated at a temperature around, or greater than, the melting points of the target plant materials. For example, in modes of practice, processing can be performed at a temperature of about 50° C. or greater, about 55° C. or greater, about 60° C. or greater, such as in the range of about 50° C. to about 85° C., or about 60° C. to about 85° C. In other modes of practice, the system is operated at temperatures below the melting point of the target compound. For example the system can be operated at about −30° C., which can minimize certain materials, such as chlorophyll. Optionally, some solvent, such as ethanol, can be added to the system to increase the fluidity at these lower temperatures. Other processing temperatures can be in the range of about 20° C. to about 60° C., particularly when steps are taken to remove materials such as chlorophylls during processing.

The method of the disclosure can also include introducing steam at one or more steps. Steam-generating equipment, including a steam injector, can introduce steam into one or more of various equipment pieces of the system, such as the mechanical processor as described herein. For example, a steam injector can introduce steam at one or more points of the mechanical processor that includes the auger, such the plant feed, the transition area, or metering area.

Processing of plants in the mechanical processor can be performed as a batch process, a semi-continuous process, a continuous process, or combination thereof.

Referring back to FIG. 1, the mechanical processor 18 can have a conduit 40 for the removal of plant material such as fiber that is separated from the surfactant composition with lipophilic plant material. Storage container 42 can collect this plant material which can be discarded or can be used for other processes (e.g., as feed materials for livestock, or for cellulosic fermentation).

The mechanical treatment step results in a liquid output that includes the liquid extraction medium, with target plant materials and non-target plant materials contained in the liquid extraction medium, e.g., dissolved in surfactant of a non-aqueous phase of the liquid extraction medium. Other plant materials that are not removed as plant fibers from the plant processor may also be present in this liquid composition, but some or all of them may be removed in subsequent processing steps such as by filtration or using chemical treatment. For example, some plant materials that are not the lipophilic plant material can be fine suspended solids that can be removed by filtration.

This fluid composition produced by mechanical processor 18, surfactant composition with lipophilic plant material, can be moved from the mechanical processor 18 to a holding container 46 through conduit 44. The holding container can collect the fluid composition and maintain desired conditions (e.g., desired temperature, with agitation) to facilitate further processing.

The system can include a container in which the fluid composition, can be swirled, or treated by "cyclonic mixing"

(not shown in FIG. 1). The principles of cyclonic mixing are known, and have been used to mix various types of materials (e.g., see U.S. Pat. Nos. 2,456,097, 4,790,666, 6,481,883). Cyclonic mixing can promote the coalescing and growth of oil droplets once the pH is lowered, and thereby improve the overall separation process.

The system can include one or more containers that are referred to as "risers" or "towers" (not shown) in which materials from the composition containing surfactant and lipophilic plant material can be affected by gravity. For example, in a composition treated to precipitate chlorophyll, the reacted chlorophyll can sink and the coalesced oil droplets can rise in the riser or tower. Oil can be removed off the top using an electrical conductivity probe, which can sense the accumulation of oil and set the rate of oil removal. At the bottom of the riser or tower a light sensor can be used to sense the presence of sediment such as chlorophyll and set the rate of removal. Oil from an upper portion of the riser or tower can be removed and transferred to a second riser or tower to further refine the oil-containing composition.

The surfactant composition with lipophilic plant material can then be moved through conduit 48 through filter to remove particulates or other material desired to be removed from the target (e.g., lipophilic) plant material. The filter can be backflushed and the filter retentate can be moved through conduit 52 to waste container 54. An exemplary filter construction includes triangular stainless steel wire spiral wound around a cylindrical or conical scaffold or frame.

The filtered surfactant composition with lipophilic plant material can then be moved through conduit 56 and into blending container 62. In some modes of practice, from supply container 58 can be delivered through conduit 60 to blending container 62 a chemical such as an acid, a metal halide, or combination thereof. The chemical can be one to reduce the pH of the composition, treat the composition to remove certain components, such as chlorophyll. Optionally, if an acid is delivered, it can be one used in an amount to reduce the pH of a the surfactant composition with lipophilic plant material, such as a pH below 7, below 6, in the range of about 1 to about 6, or in the range of about 3 to about 6, or from 3 to 4. Acid added at this processing stage, to a composition that is in the form of an emulsion, may convert the composition from an emulsion to phase-separated liquid, e.g., that contains an aqueous phase and a non-aqueous phase. The non-aqueous phase is an oil phase that contains surfactant, for example amide surfactant or high KB surfactant, with target plant material dissolved in the surfactant; this non-aqueous phase, and certain derivatives thereof, can be considered plant extract compositions as also described herein.

Examples of inorganic acids, include, but are not limited to, hydrochloric acid, hydrobromic acid, phosphoric acid, sulfuric acid and perchloric acid. Example of organic acids include, but are not limited to acetic acid, formic acid, oxalic acid, maleic acid, tartaric acid, citric acid, succinic acid or malonic acid, D-lactic acid, L-lactic acid (lactate), fumaric acid, malic acid, succinic acid, ascorbic acid, lactic acid, adipic acid.

In some modes of practice a chemical is delivered to cause the removal of chlorophyll which can be present as an unwanted contaminant in the composition with surfactant and lipophilic plant material. When the iron compound-treated composition is delivered to the electrolysis unit as described herein, an oxidation reaction occurs which results in the replacement of magnesium in chlorophylls with $Fe^+$. The addition of iron chloride ($FeCl_3$) forms oxidized iron species: the $Fe^{2+}$ ion (ferrous ion) and $Fe^{3+}$ ion (ferric ion) are oxidized states of iron that are able to associate with chlorophyll. Iron-modified chlorophyll able to be precipitated and removed during centrifugation as described herein.

The surfactant composition with lipophilic plant material (e.g., plant material extract) can be passed through conduit 62 to a portion of an electrolysis unit 66. In particular, the surfactant composition with lipophilic plant material can be passed to an anode chamber 68 of an electrolysis unit. In the anode chamber 66 the surfactant composition with lipophilic plant material can be treated under conditions to lower the pH of the composition through generation of hydrogen ions. The composition can be treated in the electrolysis unit for a desired period of time, such as about less than 4 hours, less than 1 hour, less than 40 minutes, less than 30 minutes, or preferably less than 20 minutes. Electrode materials such as copper, graphite (i.e., carbon), platinum, brass, titanium, and silver can be used, with a preferred material being platinum. The area of the electrode can vary depending on the size and configuration of the electrolysis unit, but in some arrangements the electrode can have an area in the range of about 4 to about 16 meter$^2$ on each side. The electrolysis unit 66 can be divided with a semipermeable, cationic and/or anionic permeable membrane of a desired pore size, defining the anode chamber 68 and cathode chamber 70. Exemplary membranes that can be used as the barrier include those under the tradename Nafion™ which are made from sulfonated tetrafluoroethylene-based fluoropolymer-copolymer materials.

The electrolysis unit can have any desired arrangements of components, but in some arrangements, the electrode and membrane are separated by a distance in the range of about 2 mm to about 10 mm. Space between the membrane and the electrode can be partially or fully filled with conductive, partially conductive, or non-conductive beads, such as those made from polymeric, resin, or metallic materials, or combinations thereof. The electrolysis unit can also be in the form of an electrocell with multiple plates in a battery-like stack alternating anode and cathode with a membrane between each. The electrolysis unit can be vented to remove evolved $H_2$ gas at the cathode, and $O_2$ gas at the anode.

Electrolysis of the composition can be conducted at a desired current and voltage, using electrolytes such as $FeCl_3$, ferrous sulfate, and K+(which are residual from the recycle of KOH), Li+, Na+, Rb+, such as current rates in the range of about 1-3 amperes per cm$^2$ of electrode at a voltage in the range of 1-3.5 V. Preferred operating conditions are in the range of 1.3-1.7 V and 1.2 amps per cm2 using conductive beads.

Additional chemicals may be included in the processed liquid to facilitate the process or to protect target materials from electrolytic reduction or oxidation. Examples include oxidization inhibitors as well as solvents that exhibit a high electrical conductivity.

As an example of a high conductivity solvent, propylene carbonate (PC) is an aprotic solvent with a high electrical conductivity, high-dipole moment, and high permittivity. Dimethoxyethane (DME) is a low viscosity solvent that can be effective with PC in an electrolysis process. These two solvents, may be used separately or in combination, i.e., a blend of PC and DME, in a process liquid during electrolysis of a composition as described. The blend remains acceptably non-viscous. Alkali may also be added to the composition being processed by electrolysis, e.g., KOH, LiOH, RbOH, NaOH or another.

Treatment in the anode chamber 68 of the electrolysis unit 66 causes the pH of the processed plant composition to become lowered, thereby affecting the functionality of the pH-dependent surfactant. For example, if pH has not previously been reduced to below 7, the anode chamber can cause the pH to be lowered to 7 or below, below 7, at a pH in the range of about 1 to 7, and preferably below about 6.5, below about 6.0, such as in the range of about 3.0 to about 4.0 or 6.0. At the lowered pH the pH-sensitive surfactant a) partially or fully loses its ability to emulsify lipophilic and hydrophilic components in the processed plant composition, b) partially or fully disassociates with the lipophilic plant material, c) is chemically cleaved into two or more surfactant by-product, or any combination of a)-c). At this lowered pH, the pH-sensitive surfactant, or a product thereof, is therefore more easily able to be physically separated from the lipophilic plant material. In turn, a subsequent separation step such as using a centrifuge, can be efficiently carried out.

Next, and optionally, the "pH-lowered composition" (which may also be considered a "plant material extract" as described herein) can be further treated with a chemical. The pH-lowered composition can be moved from the anode chamber 68 of the electrolysis unit 66 through conduit 72 and into treatment container 74. Optionally, one or more chemical flocculants, coagulants, sequestrants/chelating agents, or a combination of such can alter the composition by effecting precipitation or sedimentation of by-products or non-target chemical species such as iron-chlorophyll, or processing ingredients such as cationic compounds or anionic compounds, which may adversely affect deactivation or reactivation of the surfactants, from the extraction fluid. Examples of flocculants include but are not limited to anionic or cationic polyamines, DADMACS or polyDADMACS as they may be called. Examples of coagulants include but are not limited to ferric sulfate, ferrous sulfate, ferric chloride, ferrous chloride, aluminum hydroxide and aluminum sulfate. Examples of sequestrants and chelating agents include but are not limited to sodium gluconate, potassium gluconate, glucono delta-lactone, sodium hexametaphosphate, sodium tripolyphosphate, calcium acetate, calcium chloride and sodium or calcium salts of ethylene diamine tetra-acetate (EDTA). After collection and separation of the sedimented flock from the process stream, deflocculants, including, but not limited to, sodium silicate, may be used to re-disperse and recover the contaminants or by-products, if desired.

After the optional chemical treatment, the pH-lowered composition is delivered through conduit 80 to an optional separator unit 82. A preferred separator unit 82 is a centrifuge. Exemplary centrifuges that can be used for separation include those from Alfa Laval (Sweden) which typically have a series of about 35 to about 65 conical plates that spin at rates of about 6,000 to about 8,000 rpm, 12,000 rpm, or higher. During centrifugation, lighter oil fractions can be ejected through a port. Centrifuges suitable for separation of the plant lipophilic material (i.e., a non-aqueous phase of multi-phase liquid produced by breaking an emulsion form of the liquid extraction medium) can be two-phase (liquid/liquid) centrifuge or three-phase (solid/liquid/liquid) centrifuge, where the solid is heavier than water. A continuous three-phase centrifuge can be useful for removal of flocculated iron-containing materials, such as iron-chlorophyll. Three-phase centrifuges can be obtained from GEA Mechanical Equipment GMBH (Germany) and are described in documents such as U.S. Pat. No. 8,523,749 (Sep. 3, 2013), and European Patent No. 1,480,754B1 (Apr. 28, 2010). In some arrangements, the system can include more than one separator unit, such as a second centrifuge that is a decanter centrifuge to remove flocculated iron-chlorophyll as described herein.

Centrifugation produces a lighter lipophilic material-containing phase (an oil or non-aqueous phase, which is also considered a "plant material extract"), and a heavier aqueous surfactant-containing phase (e.g., the surfactant being pH-sensitive surfactant). The lighter, lipophilic material-containing phase can then be moved through conduit 84 into lipophilic material storage container 86. The lipophilic material-containing phase can be subjected to further treatment, if desired, and as discussed further herein.

The heavier aqueous surfactant-containing phase can be moved through conduit 88 and through filer 90 to remove any remaining precipitated contaminants or by-products, and into treatment container 92. Next, and optionally, the surfactant-containing phase can be further treated with a chemical. A chemical such as, potassium hydroxide or sodium hydroxide, can be delivered from chemical supply container 94 through conduit 96 to treatment container 92. The base chemical can alter the composition by reactivating the surfactant.

The electrolysis unit 66 can reduce the overall amount of base needed to reactivate the surfactant, which is beneficial as excessive cation (otherwise provided by the base) can impair surfactant function. Further, a percentage of aqueous composition (e.g., about 20-40%) can be run through an ion exchange filter, dialysis apparatus, reverse osmosis apparatus, or combination thereof, to remove anions and cations. The cation removal can take place after the pH of the composition is raised, e.g., to an elevated pH as discussed herein. This system of the disclosure can also include apparatus and mechanisms to automatically backflush and regenerate, similar to filter back-flushing described herein, when sensors detect decreases in processing efficiency and can activate back-flushing. The system can be multipart, e.g., two part, where one part can be back-flushed while the second part is active.

The base can increase the pH of the composition to regenerate the surfactant. For example, the pH can be raised to above 7, above about 7.5, and preferably above about 8.0, above about 8.5, above about 9.0, such as in the range of about 9.0 to about 13, or about 10 to about 13. Exemplary bases that can be used at this point include inorganic and/or organic bases as described herein.

The aqueous surfactant-containing phase can be passed through conduit 98 to a cathode chamber 70 of an electrolysis unit 66. In the cathode chamber 70 the aqueous surfactant-containing phase can be treated under conditions to increase the pH of the composition through generation of hydroxide ions. Electrolysis conditions are described herein.

After treatment in the cathode chamber 70 of the electrolysis unit 66, the pH of aqueous surfactant-containing phase is increased, thereby regenerating the functionality of the surfactant. For example, the cathode chamber can cause the pH to be raised to above 7, above about 7.5, and preferably above about 8.0, above about 8.5, above about 9.0, such as in the range of about 9.0 to about 13, or about 10 to about 13. At the elevated pH, the surfactant can regenerate and regain its functionality so it can be used in a subsequent cycle of plant extraction.

The regenerated surfactant can then be moved from the cathode chamber 70 through conduit 100 to tank 102. Unused water from tank 102 can be moved through conduit 104 to container 106. Water conduits 114a and 114b can also transport water tank 102 to filters 50 and 90, if back-flushing of the filters is desired. The regenerated surfactant can then be moved from tank 102 through conduit 108 to dialyzer unit 110. In the dialyzer unit 110 the regenerated surfactant can be treated to remove ionic species, such as those from the addition of acids, metal chlorides, and bases, added during steps of the processing cycle. The dialyzer unit can be one or more of an ion-exchange or reverse osmosis unit that removes ions from the surfactant composition. In certain arrangements the dialyzer unit 110 can be part of slip stream that diverts a certain amount of regenerated surfactant for ion removal from the system. For example, the slip stream can divert an amount of regenerated surfactant in the range of about 10% to 50%, or about 20% to about 40% from the system flow. The amount of ions present in the regenerated surfactant can be monitored by EC or ISE. Dialyzed regenerated surfactant can then be moved from the dialyzer unit 110 through conduit 112 back to tank 22. The regenerated surfactant can then be used in another round of extraction according to methods described herein.

References are been made to patents and printed publications throughout this specification. Each of the cited references and printed publications are individually incorporated herein by reference in their entirety.

Embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein.

Example 1 (Comparative)

As a comparative example, sodium laurel sulfate was used a surfactant.

Example 2 (Comparative)

As a comparative example, 2-butoxy-2-ethanol was used a surfactant.

Example 3

Extraction of CBD from hemp was performed. The principle target plant material from hemp was CBDA. Sectioned hemp material was used as the plant for CBD extraction, and predicted to contain 10% concentration of target plant materials (cannabinoids and terpenes) by weight on a dry basis. The moisture level of the plant was about 5% (wt). The extract was predicted to contain incidentally about 40% of plant fatty acids.

The surfactant for extraction of the target materials was a blend of non-ionic Dow Triton RW-20 and RW-50 in equal parts of 3% (wt) each in water. Another surfactant formulation that is used is RW-150 by itself or with another surfactant. The pH of the surfactant-containing extraction fluid was adjusted to about pH 11 with potassium hydroxide. Water content in the plant (5%) was taken into account for extraction. Surfactant-containing extraction fluid and plant were mixed at a 4 to 1 weight ratio (e.g., 8 pounds surfactant-containing extraction fluid to 2 pounds hemp). The surfactant-containing extraction fluid temperature was set to about 60° C. and extraction was carried out at this temperature. A temperature of 60° C. is sufficient to exceed the melting points of the target plant materials.

The hemp plant was blended with an auger-containing extractor using the surfactant-containing extraction fluid (e.g., liquid extraction medium) under mixing and compression conditions (600 psi) sufficient to release the target plant material. The extracted liquid containing extraction fluid and target plant materials was separated from the bulk of the fibrous plant material through a matrix of small ports in the auger barrel. The fibrous matter was ejected from an orifice at the nose of the auger barrel.

The extracted liquid was then treated with phosphoric acid (75%) is used to acidify the liquid to a pH of about 3. Ferric chloride, used in the range of 10-25 grams per pound of extracted liquid, was also added and a few minutes later an anionic polyacrylamide flocculant, used in the range of 1-10 milligrams per pound of extracted liquid, was added to promote the precipitation of chlorophylls and other anionic and cationic contaminants. Approximately 25 minutes of delay was allowed by the use of two 10 foot tall 12 inch diameter riser tanks/columns. In this example both sedimentation in a settling tank and centrifugation were used to remove precipitates (filtering and electrostatic attraction can also be used).

After reducing the pH, the lipophilic plant material was separated from the hydrophilic material (water, surfactant) using the riser columns and by centrifugation. The water/deactivated surfactant was filtered once again to remove any remaining flock or precipitated particles. In both cases, filtering was multi-stage, first at the 125 micron level and secondly at the 20 micron level.

The surfactancy of the liquid containing water and surfactant was restored by raising the pH of the liquid to pH 11 using potassium hydroxide.

The extraction liquid was reused in a subsequent extraction cycle. After 4 or 5 cycles, potassium and other ions increase in the extraction fluid and these are removed using an ion-exchange, dialysis, or reverse osmosis. Ion removal can also be accomplished by slip-streaming about 30% of the extraction fluid through the ion-exchange system each cycle. The level of ions is monitored with EC and ISE.

Downstream Processes

A plant extract composition as described may be prepared by any method that will result in a composition that contains ingredients of a plant extract composition as described. One particular example of a method useful for preparing a plant extract composition is a chemical extraction process as described. Other examples may include various alternate chemical processing methods or chemical extraction steps.

Once prepared, the plant extract composition can be processed by one or more of various plant extract composition processing steps (sometimes referred to as "downstream processing steps") that are designed to isolate and concentrate one or more desired target compounds present in the plant extract composition, and separate the target plant compound or compounds from other non-target compounds also present in the plant extract composition.

As presented herein, a plant extract composition is a liquid that contains a concentrated amount of one or more desired ("target") plant materials (a.k.a., "target compounds" or "target plant compounds") dissolved, emulsified, suspended, or otherwise contained in a liquid that contains surfactant (any type as described herein), optional hydrotrope, and other possible processing ingredients. Example surfactants are described herein, and are sometimes referred to as "high KB surfactants," "amide-based surfactants," "pH-dependent surfactants," and detergent-type surfactants. Depending on the stage of processing, and previous processing history, the plant extract composition may also include some portion of dissolved water as well, additives used as processing ingredients and described herein, and endogenous plant materials such as chlorophyll or other non-target plant materials that may desirably be removed by a downstream process step.

One example of a non-target endogenous plant material that is desirably removed is chlorophyll. A desired step of processing a plant extract composition that contains a substantial amount of chlorophyll is to remove the chlorophyll. The method of removing chlorophyll may be any useful method.

Example plant extract compositions at early to middle stages of processing, e.g., after being separated from an aqueous phase of a liquid extraction medium, will contain unacceptably high levels of chlorophyll or chlorophyll derivatives. If desired to reduce an amount of chlorophyll (including derivatives) in a plant extract composition before proceeding to a steps of washing and phase-separating a target compound (e.g., by oiling-out or crystallizing), a chlorophyll removal step may be performed by any useful technique.

As an example, an unwashed plant extract composition (as described, e.g., a non-aqueous phase of a liquid extraction medium, separated from an aqueous phase of the liquid extraction medium) can be added to a vessel. The plant extract composition contains a high level of the target compound CBDA, e.g., up to or greater than 10, 20, 30, or 50 weight percent, or higher (based on total weight unswashed plant extract composition), and may contain a substantial or high level of a high-kB surfactant such as Ninol CAA, M10, or Met10U. The extract is alkalinized to pH 10.3 with an alkali (e.g., KOH, LiOH, NaOH, or the like) in a concentration from 0.1, 1, 4, up to 12M, depending on the desired water present in the final mixture. (The extract may be heated or chilled. A heated extract is more likely to release phytol from the chlorophyll derivative, which may be desirable or not depending on the desired end product.)

If chilled, a chilled solution (e.g. to 20, 10, 5, 1 or below 1C) can be combined with a portion of similarly chilled propylene carbonate equal to the weight of the extract (not including added alkali solution), and the combination is vortexed or otherwise mixed thoroughly while maintaining the desired temperature. The mixture is then acidified to a pH 6, 4, 3, 2, 1 or lower, preferably pH 3, e.g. with H3PO4, HCL, formic acid, acetic acid, or another organic or inorganic acid in concentration of 0.1, 1, 4, up to 12M. The resulting solution is vortexed or otherwise mixed thoroughly and subsequently centrifuged while maintaining the desired temperature. Two phases are evident. For a target compound of CBDA, a concentrated amount of CBDA is obtained in high proportion in the bottom of the vessel, having a level of chlorophyll or derivatives that is reduced to a small fraction of an original amount, e.g., reduced to a level that is 50 percent, 20 percent, 10 percent 2 percent, or less than 1 percent of an amount present in the unwashed plant extract composition. This step may be performed in a batch or continuous (e.g. LLE) process, one or multiple times depending on the desired end product.

Examples of plant extract compositions can contain: a relatively high amount of target compound, an amount of surfactant (e.g., high KB surfactant, amide-based surfactant, pH-dependent surfactant, detergent-type surfactant, or another), dissolved water, and a low or minor amount of other ingredients that include dissolved or suspended non-target compounds such as non-target lipophilic plant materials.

The presence of water in the plant extract composition may be maintained or optionally mitigated to an advantageous level for a specific downstream process, using any method of water removal, e.g. evaporation, absorbance using molecular sieves (powder, beads or any other form) or absorbance by a hydrophilic media such as a hydrophilic membrane.

Depending on expected downstream processing, a plant extract composition, before or after a step of removing chlorophyll, may be dried to remove a substantial amount of water from the composition. A drying step may be performed, for example, after removing chlorophyll, and before (e.g., directly before) a step of phase separating liquid or solid target plant compound from the plant extract composition. Drying may be accomplished by any useful method of drying a liquid, i.e., removing water from a liquid. Examples of common techniques include the use of a molecular sieve (powder or beads), adsorption or absorption techniques, and evaporation techniques, among others. By one of these techniques, the plant extract composition may be dried remove substantially all water in the composition, e.g., such that the composition contains not more than 2, 1, or 0.5 weight percent water based on total weigh plant extract composition. Following a drying step, a step of phase separating liquid or solid target plant compound from the dried plant extract composition may be performed by any method, such as by a distillation or any other method).

While some or much of the following description of "downstream" processes is presented in terms of a method for isolating a cannabinoid (e.g., CBDA or CBD, THCA or THC, CBGA or CBG, CBCA, CBC or any other cannabinoid or a derivative) as a target compound or compounds as part of a plant extract composition derived from hemp, the described processes can be applied to other types of plant extract compositions that contain other target compounds (including any described herein), that contain any of a variety of non-target compounds, and that are derived from other plant materials.

A plant extract composition that is a product of a chemical extraction process as described herein, e.g., when the process is used to extract cannabinoid compounds from hemp, can contain cannabinoid (e.g. acid cannabinoid, base cannabinoid) as a target compound, in combination with a variety of endogenous (to the hemp plant) plant materials (e.g., chlorophylls, non-cannabinoid terpenes, plant fatty acids, saccharides, polysaccharides, waxes, proteins (generally denatured and present primarily in the aqueous phase or entrained aqueous fraction within the plant extract composition), and other naturally occurring plant compounds), pesticide or fungicide (present on a solid plant material), as well as various residual processing ingredients such as an acid, base, one or more surfactants, and other additives that facilitate efficient chemical extraction of target materials from solid plant material.

In some cases, hemp may contain unacceptable levels of certain heavy metals. Optionally, the upstream or downstream process may contain appropriate additives (e.g. salts, hydrotropes, solubilizers) and chelators, e.g. disodium-EDTA, to facilitate the chelation of heavy metals. These may be removed by a process of coagulation and flocculation described herein.

A plant extract composition may contain various biological by-products of a plant, which may include toxins, microtoxins, fungal spores, heavy metals, pathogens, among others, which are preferably removed. The present methods of processing plant extract compositions in a water-based medium that may be used with one or more of a surfactant, chelating agent, coagulant, flocculant, etc., as described, can be effective to remove these biological materials.

The residual processing ingredients may include: an emulsifying surfactant (e.g., a pH-dependent surfactant); a high KB surfactant or amide-based surfactant (e.g., Met10u, Met10, Ninol CAA, or the like); a detergent-type surfactant; a corrosion or oxidation inhibitor such as sodium borohydride (NaBH4); an oxygen sequestrant; other sequestrants or chelating agents such as disodium-EDTA; a buffer such as sodium carbonate, sodium bicarbonate, or the like; one or more alkalinizing compounds such as NaOH, KOH, LiOH; an acidifying compound such as H3PO4, an organic acid such as formic or acetic acid, a mineral acid such as phosphoric acid or HCl; a fraction of dissolved water (15% in the case of Met10u as the high KB surfactant); a salt of any kind such as ammonium sulfate, calcium chloride, salts of iodine and tin, NaCl, KCl, LiCl, NaBH4, or sodium hexametaphosphate among others; a solubilizing agent such as glycerol carbonate or propylene carbonate; among others; hydrotropes such as urea, thiourea, sodium xylene sulfonate, among others. Many general and specific types of these residual processing ingredients are described hereinabove with respect to example chemical extraction processing techniques.

Example plant extract compositions may contain an amount of surfactant that is effective to contain (e.g., dissolve, emulsify, disperse, or suspend) a useful or advantageously high amount of one or more target compounds. For cannabinoids (e.g., CBD or CBDA) as a target compound, a useful surfactant may be a surfactant that is a high KB surfactant or that is an amide-based or sulfonated surfactant, as these are described herein. The plant extract composition may also contain one or more other types of surfactant, e.g., a surfactant that functions as an emulsifier, such as a pH-dependent surfactant of the present description, or an optional hydrotrope having an activity that may can be affected or controlled by dilution (active at a 2M concentration in a composition, inactive at a concentration 0.6M and below). In example plant extract compositions, a useful or preferred amount of surfactant (e.g., a high KB surfactant, an amide-based surfactant, or an emulsifying (pH-dependent) surfactant, a "detergent" type surfactant, alone or in combination) may be in a range from a critical micelle concentration (CMC) of a particular surfactant (which may typically be 0.1 weight percent or below) to 99 weight percent, e.g., from 5, 10, or 20 weight percent, up 30, 50, 60, 70 or 80 weight percent, based on total weight plant extract composition.

According to these or other embodiments, a useful or preferred plant extract composition may also contain an amount of water. Examples of amounts of water in a plant extract composition may be in a range from 1 to 25 weight percent, e.g., from 2 or 5, up to 10, 15, or 20 weight percent water based on total weight plant extract composition.

A plant extract composition may contain an amount of water that is sufficient to allow the solution to have a measurable pH value. A pH of a plant extract composition may be any useful pH, with examples of useful or preferred pH values of a plant extract composition being in a range from 2 to 13, e.g., from 3, 4 or 5, up to 8, 9, 10, 11, or 12.

Useful or preferred plant extract compositions may contain a relatively low amount of exogenous oil, exogenous organic solvent (meaning oil or solvent that not derived from and an original chemical constituent of the plant material from which the target compound was derived), or both. Example amounts of exogenous oil, exogenous organic solvent, or a combination (total amount) of these in a plant extract composition may be less than 5, 2, 1, 0.5, or 0.1 weight percent exogenous oil, exogenous organic solvent, or a combination thereof, based on total weight plant extract composition.

A plant extract composition will contain a useful or relatively high concentration of dissolved plant material, e.g., dissolved lipophilic plant material that includes target compound and a variety of non-target materials (non-target compounds). Examples of useful or preferred plant extract compositions are capable of containing at least 1, 5, 10, or 15, and up to or in excess of 10, 20, 30, 40, 50 60, 70, 95, or 99 weight percent dissolved plant material (combined target compounds and non-target compounds) based on total weight of the plant extract composition. Preferred plant extract compositions may contain at least 5, and up to or in excess of 10, 20 30, 40, or 50 weight percent dissolved target plant material (e.g., cannabinoid such as CBD or CBDA, a target terpene or terpenoid compound or terpenoid compounds, etc.) based on total weight plant extract composition.

With respect to hemp as a solid plant material and CBD or CBDA as a target compound, the amounts and types of plant materials contained in a plant extract composition (prepared by any method) can depend on the source of the plant materials, as well as processing steps used to prepare the plant extract composition (which may be determined or affected by the source of the plant materials). A relatively lower amount of non-target chemical compounds may be present in a plant extract composition derived from hemp that is: fresh (less aggressive surfactancy required); clean (free of dirt, inoculants, pesticides or heavy metals); and that has lower salt or pH buffer capacity (dependent on cannabinoid content, strain, soil minerals, and fertilizer). For example, if an initial hemp source of the plant material contains a relatively lower amount of CBDA, a higher total amount (pounds) of the hemp will be required to produce a given amount (pound) of cannabinoids. This means that a higher relative amount of non-target plant components such as minerals, chlorophyll, fatty acids and non-target terpenes, along with a higher relative amount processing additives (e.g., surfactants, chelating agents, acid, base) may be present in a plant extract composition, and one or more, possibly all, must be removed in processing, depending on the desired final product.

Hemp, when harvested, contains principal cannabinoids in their acid form with a small fraction (usually 2-15%) of cannabinoids in base form. If the hemp is stored, depending on storage conditions (heat, moisture, oxygen, pH) this fraction of base cannabinoids can increase. A plant extract composition may contain a variety of non-target (unwanted) chemical materials that need to be removed or reduced to proceed with downstream processing that produces a purified concentrated form of target compound. Non-target chemical materials include salts, heavy metals, pesticides, water soluble or flocculated color components, and other impurities. Heavy metals are sometimes present as a component of an organic compound, like methyl mercury chloride (MMC). Such compounds may be water soluble or oil soluble or insoluble depending on the associated moiety. MMC is soluble in organic solvent such as acetone and alcohols, but only sparingly soluble in water.

Once produced, a plant extract composition may be processed by chemical processing steps that will isolate and concentrate a target compound. A chemical processing step may be one that: removes a non-target compound or compounds from a liquid; removes (e.g., extracts) target compound or compounds from a liquid; that selectively increases or decreases solubility of a target compound or a non-target compound in a liquid solution or a phase of a liquid composition; or that otherwise effects chemical removal or isolation of a target compound or a non-target compound from a liquid.

One example of a type of chemical processing step that may be used to process a liquid plant extract is a liquid-liquid solvent extraction step, to remove non-target compounds from a solution that contains target compounds and non-target compounds. In this type of step, an organic solvent (which may be referred to as a "differential solvent") is contacted with a plant extract composition to cause non-target compound from the plant extract composition to become dissolved in the differential solvent and to be removed from the plant extract composition. As a single example, D-limonene has a high affinity for some monoterpenes that may be present in a plant extract composition derived from hemp as non-target compounds, but low affinity for CBDA under similar conditions (e.g., cold, at a reduced temperature). D-limonene may be used as a "differential solvent" to separate (remove) non-target terpene compounds from the plant extract composition and from CBDA contained in the plant extract composition.

Another example of a processing step is a step of combining a liquid that contains target compound with antisolvent. When a target compound is contained in a liquid, e.g., an organic solvent or water (together, "solvents"), an anti-solvent may be used to reduce the capacity of the solvent to contain the target compound, thereby supersaturating the solvent with the target compound. An anti-solvent is a compound with high affinity for the solvent but much lower affinity for the target compound. An example of a useful processing step is to process a plant extract composition or a derivative thereof with one or more anitsolvents. The use of an antisolvent can increase the efficiency of purification of a target compound by increasing the saturation of one or more target compounds in a solvent to which the target compounds are added or present. The antisolvent occupies the binding potential of a primary solvent for a target compound, thereby reducing the ability of the primary solvent to contain (e.g., dissolve) the target compound. For example, CBDA is very soluble in DMDA (over 1000 mg/ml DMDA at 70C); mineral oil has significant solubility in DMDA (about 30%), but CBDA has significantly lower solubility in mineral oil (only about 6 mg/ml under certain conditions). Mineral oil may be used as an anti-solvent, under certain conditions, to create higher saturation of CBDA in DMDA, without much loss of yield or efficiency. A similar effect can be occur by using glycerol carbonate or propylene carbonate in place of mineral oil. The antisolvent may also have usefulness for dissolving certain non-target compounds such as chlorophyll derivatives, pheophytins, pheophrbides and chlorophyllins, thereby improving the partitioning of non target compounds from target compounds.

Optionally, a coagulant may be used to coagulate particulate matter that may be present in a plant extract composition. A flocculant may then be used to agglomerate and precipitate the coagulated particles. A sequestrant, a chelation agent, or both, may be used to remove other organic and inorganic materials at certain stages of purification or processing of a plant extract composition.

Another example of a type of plant extract composition processing step is a step of washing the plant extract composition with an aqueous medium to remove hydrophilic materials from the plant extract composition, to thereby separate the hydrophilic materials from the plant extract composition and the target compound that remains dissolved in the plant extract composition. Removing salts, water soluble "additives" (such as EDTA, and residual water-soluble surfactants, among others), and natural colorants, is an example of compounds desirably removed from a plant extract composition. Multiple washes, e.g., from 1 to 15 washes, may be useful or required. The aqueous medium may preferably be a low-temperature acidic aqueous solution that has a comparatively low affinity for dissolving a target compound, and a relatively higher affinity for dissolving certain non-target compounds (e.g., hydrophilic compounds) contained in the plant extract composition.

The solubility of cannabinoid target compounds in water can be substantially affected by pH and by temperature. The solubility of acid cannabinoids in water can vary over more than 3 orders of magnitude by manipulating temperature and pH of a water solution. At a temperature of 70 degrees Celsius or higher, and pH of 10 or higher, the solubility of CBDA in water is over 20 milligrams per milliliter. Conversely, at a temperature of 4 degrees Celsius or lower and pH 4 of or lower, the solubility of CBDA in water is below 20 micrograms per milliliter. Consequently, a process of washing a plant extract composition that contains CBDA with acidified water having a low temperature can be effective to remove hydrophilic components from the plant extract composition, without removing much CBDA from the plant extract composition.

The water used to wash the plant extract composition can be an acidic wash water that contains a relatively high amount of water, and optionally one or more chemical additives to improve the solubility of non-target (e.g., hydrophilic) compounds in the acidic wash water, and that reduce the solubility of desired target compound (e.g., CBDA) in the acidic wash water. Examples of such additives include chelating compounds such as solubilizing agents, hydrotropes, one or more salts, hydrotropes, solubilizers, EDTA, flocculants, and coagulants. Specific examples of coagulants include aluminum chlorohydrate, polyaluminum chloride, polyaluminum sulfate chloride, polyaluminum silicate chloride, and different forms of polyaluminum chloride, ferrous and ferric chloride and sulfate, polymeric sulfate, and ferric salts with polymers and polymerized aluminum-iron blends. These can also be used to remove some heavy metals such as arsenic and many pathogens including viruses. Examples of coagulants include polyacrylamide flocculants, chitosan (by deacetylation of chitin), among others.

The amount of water in the acidic wash water may be at least 80, 85, 90, or 95 weight percent, based on total weight of the acidic wash water.

The type of chemical additive included in the acidic wash water may be any that will reduce the solubility of a target compound (e.g., CBDA) in the acidic wash water or increase solubility of one or more non-target compounds in the acidic wash water. Examples of useful chemical additives include surfactants (e.g., surfactants that function as a detergent), organic solvents, salts, hydrotropes, or a combination of these.

A hydrotrope may also be useful during processing of a plant extract composition, e.g., by including one or more hydrotropes in an aqueous washing composition (e.g., wash water) during a washing step. The use of a hydrotrope may potentially result in an increased loss of acid cannabinoids, and a reduction in initial efficiency, but may be overall advantageous based on a balance that includes reduced cost of processing, reduced overall time needed for processing, reduced equipment cost. Examples of useful hydrotropes include sodium xylene sulfonate, cumene sulfonate naphthalene sulfonate, p-toluene sulfonate (e.g., sodium salt), other sulfonates, toluene sulfonic acid (e.g., sodium salt or potassium salt), xylene sulfonic acid (e.g., sodium salt, ammonium salt, potassium salt, calcium salt), cumene sulfonic acid (e.g., sodium salt, ammonium salt), tosylate, and urea. An amount of a hydrotrpe included in an acidic wash water may be below 5 weight percent, e.g., below 3, or 2 weight percent, based on total weight of the wash water, e.g., to produce a wash water that contains a concentration of the hydrotrope in the water of at least 2 molar.

Another useful processing technique may be to include a solubilizing agent in an aqueous wash medium to facilitate or improve an effect of a washing step. Example solubilizing agents are described hereinabove with respect to the chemical extraction step. A solubilizing agent such as propylene carbonate can be included in an acidic wash water in any useful or effective amount, such as at an amount of below 5 weight percent, e.g., below 3, or 2 weight percent, based on total weight of the acidic wash water.

In traditional processing of hemp or cannabis, using organic solvents, plant waxes are highly dissolved. Removal of these waxes constitutes an additional processing step in the downstream that is time consuming and costly. The use of surfactants in or as a liquid extraction medium, with a reduced or minimal amount of organic solvent, significantly reduces the extraction of waxes.

Another useful processing technique may be to include a detergent-type surfactant in aqueous wash water, to facilitate or improve an effect of a washing step. Examples of surfactants that functions as a detergent are described hereinabove with respect to the chemical extraction effect. These include alkane sulfonates, e.g., sodium caprylyl sulfonate, and many other varieties of alkane sulfonates, as well as other various types of detergent-type surfactant as described herein. An amount of a surfactant (e.g., that functions as a detergent) that can be included in an acidic wash water may below 5 weight percent, e.g., below 3, or 2 weight percent, based on total weight of the acidic wash water.

The acidic wash water may also preferably be held at a reduced temperature (below 32 degrees Celsius) to reduce the solubility of a target compound (e.g., CBDA) in the acidic wash water. Examples of useful or preferred temperatures of acidic wash water may be below 20 degrees Celsius, e.g., below 10 or below 5 degrees Celsius. The use of a small amount of one or more compounds that reduce the freezing point of water, such as propylene glycol, can allow the temperature of wash water or other downstream processes to proceed at temperature close to or below the freezing point of water. For example, a 2% solution of propylene glycol in wash water or during any downstream processes involving an aqueous phase allows processing to proceed at −2C or slightly below.

A pH of an acidic wash water may be reduced and controlled by adding any useful organic acid or inorganic acid to the medium, e.g., an organic acid, a mineral acid (such as HCL). Acidifying agent can be included in the wash water in an amount that will result in a pH of the wash water that is below 6, e.g., below about 5, or in a range from 1 to 5 or from 2 to about 4.

An acid wash step of a plant extract composition may be performed in a continuous, semi-continuous, or batch process. In a continuous process (comparable to a liquid-liquid extraction process) a rate of flow of wash water and a total volume of wash water (in proportion to a rate and volume of plant extract composition) in an extraction apparatus can be selected based on properties (e.g., composition) of a plant extract composition, as well as characteristics and the purpose and goal (impurities desirably removed) of the acid wash step and any subsequent downstream processing steps (e.g., desired end purity and composition of a final concentrated plant extract product). The calculations used in a liquid-liquid extraction ("LLE") are well established and may vary with the compounds and amounts of compounds contained in the plant extract composition, compounds desirably removed from the plant extract composition, the composition of the acidic wash water, and the specific liquid-liquid extraction equipment used (example equipment types include Centrifugal, SCHEIBEL® columns, KARR® columns, rotating disc contactor (RDC) columns, pulsed columns, packed (SMVP) columns and sieve tray columns).

An acid wash step may use up to 15 volumes of acidic wash water for processing one volume of plant extract composition. In some cases, very little acidic wash water is required, such as if a plant extract composition contains a low amount of hydrophilic non-target compounds that are desirably removed, e.g., that will interfere with subsequent processing such as crystallization. In general the pH of wash water is low (1.2-5) and the temperature range is low, e.g., from 10 degrees Celsius to −30 degrees Celsius (in the case of higher concentrations of compounds in wash water).

One specific example of a batch-type acid wash step may be performed as follows. A volume of 250 milliliters of a plant extract composition is added to a jacketed 500 ml 2-neck reactor with stirring and a valve at the bottom for aqueous phase removal. The jacket is used to achieve the desired temperature using a heater/chiller. One volume of wash water (250 ml) is added with stirring for 2 minutes, the acid wash water having a pH of 2.5 and a temperature of 8 degrees Celsius. The two liquids are maintained in contact and allowed to settle for 5 minutes, after which the aqueous phase is removed. This process is repeated 8 times. Acidic agents used to reduce pH of the acidic wash water were $H_3PO_4$ (5M) and HCl (0.5M).

After an acid wash step, the washed plant extract composition contains ingredients that are comparable to the plant extract composition before the water washing step, but with many of the non-target materials, e.g., hydrophilic materials, pH dependent surfactant, converted chlorophyll derivatives, among other non-target materials, removed. At the same time, the acid washing step removes very little, e.g., a low or insubstantial amount, of high KB surfactant and acid cannabinoid.

A useful washed plant extract composition may contain a substantial amount of surfactant, especially a high KB or amide-based surfactant, or a pH-dependent surfactant that was present in the plant extract composition before the acid wash step. Example acid-washed plant extract compositions may contain a substantial amount of high KB surfactant, in a range from 15 to 95 weight percent, e.g., from 20 to 80, or from 30 to 60 or 70 weight percent, based on total weight (acid-washed) plant extract composition, and a reduced amount (relative to the pre-acid-washed precursor) of pH-dependent surfactant and salts. The plant extract composition, after the acid-washing step will still contain a substantial amount of dissolved target material such as acid cannabinoid (CBDA), although the amount may be reduced (e.g., slightly) relative to the amount of target material in the plant extract composition before the acid washing step. The amount of target compound (e.g., cannabinoid) in the plant extract composition after the acid washing step may be, e.g., in an amount of at least 1, 2, 3, 5, 10, or 15 percent by weight, based on total weight of the washed plant extract composition.

As desired, optionally, a method of further processing the acid-washed plant extract composition can include a step of adjusting the pH of the washed plant extract composition to a pH in a range from 3 to 11, e.g., to a pH in a range from in a range that is between 5 to 11, preferably from 8 to 11 or from 10 to 11.

In a subsequent step, referred to as an "alkaline washing step," the acid-washed plant extract composition is washed with alkaline (basic) wash water to remove a target compound (especially an acidic target compound such as CBDA) from the acid-washed plant extract composition, resulting in the target compound becoming dissolved in the alkaline wash water. This alkaline washing step at alkaline conditions produces an aqueous alkaline extract solution that contains a high amount of water with dissolved target compound, e.g., CBDA.

The amount of water in the alkaline wash water may be at least 80, 90, 95 parts by weight based on total weight of the alkaline wash water. The alkaline wash water is at an elevated temperature to improve solubility of the target compound in the alkaline wash water. Examples of useful or preferred temperatures of alkaline wash water may be at least 50, 60, or 70 degrees Celsius. The alkaline wash water has an alkaline pH, e.g., a pH in a range from 8 to 12, e.g., from 9 to 11.5 or from 10 to 11. The alkaline wash water may also contain a salt, hydrotrope, or both.

As an example alkaline washing step, in the same apparatus used to perform the previous acidic washing step (using acidic wash water), the acid-washed plant extract composition is washed with alkaline wash water (e.g., having a pH of approximately 10.5, by added KOH) at 70C (achieved by the jacketed flask). As with the previous acidic washing step, 2 minutes of stirring followed by 5 minutes of settling is used for each wash. Multiple washes with the alkaline wash water may be performed.

In a different example of an alkaline wash process, which is continuous, a plant extract composition (that has optionally been washed with acidic wash water) is introduced into the 'light-phase' inlet of Karr type liquid-liquid extractor at 65C. Simultaneously, alkaline wash water at pH 10.5 and 65C is introduced into the "heavy-phase" inlet of the extractor. The alkaline wash water and the plant extract composition interact within moving baffle plates of the extractor until they reach equilibrium concentrations. The alkaline wash water, saturated with target compound (e.g., CBDA) under these conditions, exits the heavy-phase outlet at the bottom of the extractor.

The alkaline wash water that contains CBDA may be processed to extract the target compound (e.g., CBDA) as an oil from the water, called "oiling-out" (discussed below). This oiling-out step may be performed multiple times to further purify or isolate the target compound. Alternately, the water may be further treated to allow the target compound to be efficiently removed from the water by a step of forming solid (crystals) of the target compound (e.g., CBDA) contained in the water. Optionally, the target compound-depleted oil (possibly containing a significant portion of DMDA) that results from the alkaline washing step, referred to as a "raffinate," exits the light-phase outlet at the top of the liquid-liquid extractor and may be processed for regeneration of and reuse of DMDA, and for further extraction of alternate desirable compounds such as terpenes.

The alkaline washing step produces an aqueous alkaline extract solution that has an elevated temperature and that contains a high amount of water with dissolved target compound, e.g., CBDA. The amount of water in the aqueous alkaline extract solution may be at least 80, 90, 95 parts by weight based on total weight of the aqueous alkaline extract solution. Examples of a useful or preferred temperature of an alkaline extract solution may be at least 50, 60, or 70 degrees Celsius. The amount of target compound, e.g., CBDA, that is present (e.g., dissolved or otherwise contained) in the aqueous alkaline extract solution can be an amount that is considered to be saturated or even super-saturated, e.g., an amount of at least 0.1, 1, 2, 3, 5, 10, or 15 percent by weight target compound (e.g., CBDA), based on total weight alkaline extract solution.

A target compound can be removed from an aqueous alkaline extract solution that contains a high (e.g., saturated or super-saturated) concentration of the target compound (at an elevated temperature) by adjusting the pH, temperature, or both, of the aqueous alkaline extract solution to cause target compound to phase separate out of the solution as a separate phase, which may be a solid phase (e.g., crystals), or a liquid phase (i.e., an oil phase). The solubility of target compounds, e.g., an acidic target compound such as CBDA, in water varies greatly with temperature and pH. Depending on the desired end-product, additives such as hydrotropes, salts, and solubilizers, as discussed herein, may optionally be used in either a crystallization or oiling-out technique to include or reject fatty acids, terpenes (terpenoids), and small amounts of high-kB surfactants that may be entrained in the aqueous alkaline extract solution containing the target compound. Manipulating temperature and pH in the course of a purification process can allow for orders magnitude changes in solubility of CBDA in water, and either a highly efficient crystallization of the target compound, or removal of the target compound as a liquid oil phase ("oiling-out") of the target compound (e.g., CBDA) from a predominantly aqueous solution.

According to an "oiling-out" technique, target compound dissolved in an aqueous alkaline extract solution (at high temperature and alkaline pH) can be separated from the aqueous solution by causing the target compound to form a separate oil phase, which can be accomplished by reducing the solubility of the target compound in the aqueous solution by reducing pH and temperature of the solution. The aqueous solution begins at a high temperature and an alkaline pH, and contains dissolved target compound (e.g., CBDA) along with optional residual ingredient such as processing ingredients from an upstream processing step. The amount of target compound may be a substantial amount, e.g., at a level of saturation, or in an amount of at least 0.1, 1, 2, 3, 5, 10, or 15 percent by weight target compound (e.g., CBDA), based on total weight alkaline extract solution. To remove target compound by phase separation, the aqueous alkaline extract solution may be cooled to a temperature below about 30 degrees Celsius, e.g., below 20, 10, or 5 degrees Celsius, e.g., in a reaction vessel or continuous transport process. If the concentration of target compound in the aqueous solution is sufficiently high, reducing the temperature of the solution can begin a supersaturation process by which the aqueous solution becomes supersaturated with the target compound. Next, the pH of the reduced-temperature solution is reduced, preferably in a rapid fashion, to an acidic pH, e.g., below 5 or 4, e.g. to a pH of approximately 3.0. With light agitation the entrained target compound separates from the water as part of an oil phase that rises to the top of the vessel or transport processor (or may alternately sink, depending on purity and density of the aqueous extract solution), where the oil phase (which contains a concentrated amount of the target compound (e.g., CBDA), e.g., at least 10, 20, 30, 50, 70, 80, or 90 weight percent target compound based on total weight oil phase) may be separated by skimming, centrifugation, collection on a refrigerated rotating drum, or any other continuous or batch oil-water separation process.

According to certain example methods, an alkaline aqueous extract solution at an elevated temperature (e.g., greater than 60 degrees Celsius) that contains a high (e.g., saturated or super-saturated) concentration of target compound (e.g., CBDA) can be processed first by an "oiling-out" step, followed by removing target compound from the oil of the "oiling-out" step using an acid washing step, and then and a crystallization step, as follows.

In a first example, using a batch process, an oil phase that is produced in an "oiling-out" step is first contacted with alkaline water at an elevated temperature to transfer target compound from the oil to the alkaline water. For example, clean water is brought to pH=10.5 and 65C in a vessel with agitation. Oil that contains a high concentration of target compound, e.g., CBDA oil produced by an oiling-out step, is combined with the water until no more oil will dissolve (i.e., the water is saturated with the CBDA oil), and oil begins to collect on the top of the water. The water phase, which is a saturated water-CBDA solution having an alkaline pH and a high temperature, is removed for crystallization, being careful not to include undissolved oil.

According to an example, a crystallization step may be as follows. An alkaline aqueous extract solution at an elevated temperature (e.g., greater than 60 degrees Celsius) that contains a high (e.g., saturated or super-saturated) concentration of target compound (e.g., CBDA) is collected in a vessel. The pH of the solution is adjusted to 10.5. The temperature of the solution is reduced to 4 degrees Celsius. Cold $H_3PO_4$ (5M) is added dropwise with gentle agitation until the pH is less than 5, e.g. below 3.0. Crystallization begins almost immediately and continues for about 10 minutes.

In an alternate process, oil produced in an "oiling-out" step is can be contacted with alkaline water in a continuous step to transfer target compound to the alkaline water for subsequent crystallization. Clean water (at pH 10.5 and 65C) enters a bottom of a dissolution column at a controlled rate. CBDA oil, from an oiling-out process above, is injected near the bottom of the column at a rate that does not exceed the saturation concentration of the water-oil solution under the given conditions. As the solution fills the column, moving baffles improve dissolution of the CBDA in the water. Temperature and pH are maintained throughout the column. An alkaline aqueous solution that contains dissolved CBDA exits the top of the column. That aqueous solution can then enter a continuous crystallizer. (Note that a location of introducing liquids into a column can depend density and relative densities of multiple liquids being introduced to the column. In general, denser liquids are introduced above the baffles but below the top exit port and lighter liquids are introduced toward a bottom but above the bottom exit port. An oil that contains a concentrated amount of target compound in a first or early stage of a series of liquid-liquid extraction steps is typically lighter than water, so will be introduced below a water phase and rise. In later extraction steps, an oil phase may be heavier than water requiring a modification to the density of the water or a reconfiguration of the LLE method or column.)

Within the crystallizer, the aqueous solution may be cooled to approximately 10F. This begins the supersaturation process. The pH of the aqueous solution is then reduced (e.g., to below 5, e.g. below 3.0) in a controlled manner to further supersaturate the CBDA in water to produce crystals at such a rate to maximize the quality and quantity of crystals produced.

As an alternative to an "oiling-out" technique followed by a crystallization step, target compound dissolved in an aqueous solution (at high temperature and alkaline pH) can be separated from the aqueous solution by causing the target compound to directly form a separate solid phase such as crystals within the solution, i.e., to "crystallize out" of the solution, without an "oiling-out" step. Depending on the composition of the aqueous solution, e.g., if the aqueous solution contains a sufficiently high concentration and purity of dissolved target compound, the target compound may be caused to form crystals directly by reducing pH and temperature of the aqueous solution. The solubility of CBDA in Met10u goes from 100% at 60C down to 1% at 0C. However, CBDA does not easily crystallize from this solution. A method as described may include adding surfactant (e.g., ninol CAA) or an oil or a solvent or additive that encourages crystallization or alternatively, oiling out.

The aqueous solution begins at a high temperature, an alkaline pH, and contains dissolved target compound (e.g., CBDA) with any residual oil droplets preferably removed (the aqueous solution may optionally contain amounts of processing ingredients as described); the aqueous solution may contain, for example dissolved target compound in a substantial amount, e.g., at a level of saturation. To remove target compound by direct crystallization phase separation, the aqueous solution may be cooled to a temperature below about 30 degrees Celsius, e.g., below 20, 10, or 5 degrees Celsius, e.g., in a reaction vessel or continuous transport process. If the concentration of target compound is sufficient, reducing the temperature can begin a supersaturation process by which the aqueous solution becomes supersaturated with the target compound. The pH of the solution is slowly reduced either as the temperature is being reduced or after the temperature has been reduced, to an acidic pH, e.g., below 5 or 4, e.g. to a pH of approximately 3.0. With light agitation the target compound separates from the water as solid crystals that may be physically separated from the solution.

The crystals may be collected, processed, and purified as desired. According to example processes, crystals of acid cannabinoids may be vacuum filtered with a 7 micron filter washed with several volumes of cold acidic water. Wash intensifiers such as hydrotropes, cosolvents (e.g., propylene carbonate, glycerol carbonate, or other organic solvents that will remove impurities with only a low or minimal loss of target compound (e.g., CBDA)), or detergents may be added to the wash water to further reduce residual compounds. Intensifiers are chosen to remove a minimum amount of acid cannabinoid from the crystalline mass. Propylene carbonate, glycerol carbonate, and sodium caprylyl sulfonate are examples of optional intensifiers.

The crystals are kept cool and may be dried by freeze-drying, cold forced air flow, cold nitrogen flushing, or vacuum drying. Without intensifiers the purity of acid cannabinoids in these crystals can be at least 95 percent by weight based on total weight crystals. With intensifiers, purity can exceed 99 by weight based on total weight crystals. If base cannabinoids are desired, this can be accomplished by heating the dried crystals to >130C or by electrolysis.

Any one or more of the downstream processes described herein may be performed multiple times to achieve a desired level of purity of the target compound or desired reduction of certain non-target compounds, e.g. high-kB surfactant.

Example 4

The following example processing steps were performed on a plant extract composition, after chlorophyll removal, to separate high KB surfactant from CBDA. The plant extract composition contained substantially CBDA and Met10U surfactant.

In one embodiment of the method of separation of Met10U from CBDA, the temperature dependent differential solubility of the acid cannabinoids, CBDA for example, in a high-kB surfactant, Met10u for example, is useful to facilitate a step of separating the two liquid materials from a liquid composition that contains both liquids in substantial amounts.

A saturated solution of CBDA in Met10u is prepared at 30C or preferably at 60C or higher, up to 100C or higher but below 130C. At a temperatures that is at least 130C, CBDA begins to lose its carboxylic moiety (decarboxylation) and become CBD. At temperatures above 130C CBD, not CBDA, could be separated if the desired end product is CBD. Though not strictly necessary, an anti-solvent with a low viscosity at temperatures at or below a minimum crystallization point or oiling-out point, may be introduced, at a temperature below the boiling point of the anti-solvent, e.g., heptane, pentane, propylene carbonate, ethylene carbonate, glycerol carbonate or a solvent that supports a low solubility for CBDA and a higher solubility for Met10u at a low temperature and having an acceptably low viscosity at a useful temperature for separation.

The amount (in percent) of antisolvent added to the saturated solution may be from 0% to 98%, in one case 24% but preferably the minimum required for low cost and high yield result. The antisolvent may be slowly added after the CBDA/Met10u mixture is introduced to an appropriate crystallizer and slowly cooled or heat cycled with mild circulation or agitation. Alternately, a reverse crystallization may be accomplished through the slow addition of CBDA/Met10u mixture to the polar solution. Sonification may or may not be used. Seed crystals may be added and the CBDA is slowly crystallized from solution.

Alternately the CBDA/Met10u mixture may be added to an alkalinized water pH adjusted between 7, 9, preferably 10.5 and 11.5 or higher, also containing propylene glycol/glycerol (glycerol in 80% proportion to propylene glycol) in enough proportion to reduce the freezing point of water to an appropriate temperature. The mixture is cooled quickly. An acid solution such as H3PO4 is introduced, reducing the pH to 5, 4 or preferably 3 or lower. The solution may then oil-out.

The invention can be defined by any one or more of the following numerically-identified examples.

Example 1. A Plant Extract Composition Comprising at least 15 weight percent surfactant,
at least 5 weight percent plant material, based on total weight plant extract composition.

2. A plant extract composition of example 1 comprising:
from 15 to 70 weight percent surfactant,
at least 20 weight percent lipophilic plant material, based on total weight plant extract composition.

3. A plant extract composition of example 1 or 2 comprising at least 5 weight percent cannabinoid, based on total weight plant extract composition.

4. A plant extract composition of any of examples 1 through 3 comprising not more than 20 weight percent water based on total weight extract composition.

5. A composition of any of any of examples 1 through 4 comprising
from 15 to 70 weight percent surfactant,
at least 20 weight percent cannabinoid,
from 3 to 20 weight percent non-cannabinoid lipophilic plant material derived from the plant material, and
from 1 to 20 weight percent dissolved water.
based on total weight plant extract composition.

6. A composition of any of examples 1 through 4 comprising:
from 15 to 50 weight percent surfactant,
from 5 to 50 weight percent cannabinoid,
from 1 to 20 weight percent non-cannabinoid lipophilic plant material derived from the plant material, and
from 1 to 20 weight percent water, based on total weight plant extract composition.

7. A composition of any of examples 1 through 6 comprising:
less than 5 weight percent non-cannabinoid lipophilic plant material, and
less 10 weight percent water,
based on total weight plant extract composition.

8. A composition of any of examples 1 through 7 comprising from 20 to 50 weight percent cannabinoid derived from the plant material.

9. A composition of any of examples 5 through 7 wherein the non-cannabinoid lipophilic plant material is one or more of: an essential oil, a plant lipid, a plant lipid oil, a plant wax, a plant resin, chlorophyll, a fatty acid, a terpene, a terpinoid, an oil-soluble vitamin, a cannabinoid aromatic compound, a flavonoid, lactone, or a combination thereof.

10. A composition of any of examples 1 through 9 comprising less than 5 weight percent exogenous organic solvent, based on total weight plant extract composition.

11. A composition of any of examples 1 through 10 comprising less than 5 weight percent exogenous oil, based on total weight composition.

12. A composition of any of examples 1 through 11 comprising cannabinoid selected from cannabinol (CBN), cannabinolic acid (CBNA), A(9)-tetrahydrocannabinol (A(9)-THC), Δ(9)-tetrahydrocannabinolic acid (A(9)-THCA), A(9)-cannabidiol (A(9)-CBD), Δ(9)-tetrahydrocannabidiolic acid (A(9)-CBDA), A(8)-tetrahydrocannabinol (A(8)-THC), Δ(8)-tetrahydrocannabinolic acid (A(8)-THCA), A(8)-tetrahydrocannabidiol (A(8)-CBD), Δ(8)-tetrahydrocannabidiolic acid (A(8)-CBDA), A(9)-tetrahydrocannabivarin (A(9)-THV), cannabigerol (CBG), cannabigerolic acid (CBGA), cannabichromene (CBC), cannabichromenic acid (CBCA), cannabicyclol (CBL), cannabicyclolic acid (CBLA), Cannabidivarin (CBDV) and Tetrahydrocannabivarin (THCV).

13. A composition of any of examples 1 through 12 wherein the surfactant is selected from: an amide-based surfactant, a high KB surfactant, a pH-dependent surfactant (e.g., a non-ionic surfactant), a detergent-type surfactant (e.g., that is amphiphilic), and a combination of two or more of these.

14. A composition of example 13 wherein the amide-based surfactant has the formula $R^4C(O)NR^5R^6$, wherein $R^4$, $R^5$, and $R^6$ are independently selected from saturated and unsaturated hydrocarbon-containing groups, and $R^4$, $R^5$, and $R^6$ have a total number of carbon atoms in the range from 6-16.

15. A composition of example 13 wherein the amide-based surfactant has the formula:

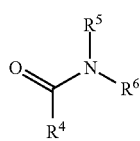

wherein $R^4$ is a saturated or unsaturated alkyl chain, $R^5$ and $R^6$ are the same or different and are saturated alkyl chains, and wherein $R^4$ has a greater number of carbon atoms than $R^5$ or $R^6$.

16. A composition of any of examples 13 through 15 wherein the amide-based surfactant comprises: N, N-dimethyl 9-decenamide, N, N-dimethyldecanamide, or a combination thereof.

17(a). A composition of any of examples 13 through 15 wherein the amide-based surfactant has a Kauri-butanol value of at least 100.

17(b) A composition of examples 1 through 12 wherein the surfactant is a non-ionic surfactant; e.g., wherein the surfactant has the formula $R^1NR^2R^3$, wherein $R^1$ is a hydrocarbon-containing group, and $R^2$ and $R^3$ are independently selected from groups comprising both oxygen and carbon atoms; e.g., wherein $R^1$ has an amount of carbon atoms in the range of 6-24, preferably 8-18, or preferably 12-14, and $R^2$ and $R^3$ are independently selected from alkoxylate groups, and preferably both $R^2$ and $R^3$ are alkoxylate groups.

18. A composition comprising of any of examples 1 through 17(b) comprising a multi-phase composition that contains the plant extract composition as one phase and a second phase different from the plant extract composition.

19. A liquid extraction medium comprising water, surfactant, and base, the medium comprising
 at least 0.1 weight percent pH-dependent surfactant, or
 at least 1 weight percent amide-based surfactant, or
 amphiphilic, detergent-type surfactant,
 or two or more of these,
based on total weight liquid extraction medium,
the liquid extraction medium having a basic pH.

20. A medium of example 19 wherein the medium is an emulsion.

21. A medium of example 19 or 20 comprising:
 from 0.1 to 40 weight percent pH-dependent surfactant, or
 from 1 to 20 weight percent amide-based surfactant,
 optional detergent-type surfactant, and
 one or more processing ingredients selected from a hydrotrope and a solubilizing agent,
 or a combination of these,
based on total weight liquid extraction medium.

22. A medium of any of examples 19 through 21 comprising less than 5 weight percent exogenous organic solvent, based on total weight liquid extraction medium.

23. A medium of any of examples 19 through 22 comprising less than 5 weight percent exogenous oil, based on total weight liquid extraction medium.

24. A medium of any of examples 19 through 23 wherein the pH-dependent surfactant is an alkylamine alkoxylate.

25. A medium of any of examples 19 through 24 wherein the pH-dependent surfactant has the formula $R^1NR^2R^3$, wherein $R^1$ is a hydrocarbon-containing group, and $R^2$ and $R^3$ are independently selected from groups comprising both oxygen and carbon atoms.

26. A medium of example 25 wherein $R^1$ has from 6 to 24 carbon atoms, and $R^2$ and W are independently selected from alkoxylate groups.

27. A medium of any of examples 19 through 26 wherein the amide-based surfactant has the formula $R^4C(O)NR^5R^6$, wherein $R^4$, $R^5$, and $R^6$ are independently selected from saturated and unsaturated hydrocarbon-containing groups, and $R^4$, $R^5$, and $R^6$ have a total number of carbon atoms in the range from 6-16.

28. A medium of example 27 wherein the amide-based surfactant has the formula:

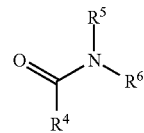

wherein $R^4$ is a saturated or unsaturated alkyl chain, $R^5$ and $R^6$ are the same or different and are saturated alkyl chains, and wherein $R^4$ has a greater number of carbon atoms than $R^5$ or $R^6$.

29. A medium of example 27 or 28 wherein the amide-based surfactant comprises: N, N-dimethyl 9-decenamide, N, N-dimethyldecanamide, or a combination thereof.

30. A medium of any of examples 27 through 29 wherein the amide-based surfactant has a Kauri-butanol value of at least 100.

31. A method of extracting material from solid plant material, the method comprising contacting the solid plant material with liquid extraction medium as recited at any of examples 19 through 30, or as otherwise described herein.

32. A method of example 31 comprising, after contacting the solid plant material with liquid extraction medium, lowering the pH of the liquid extraction medium to cause the liquid extraction medium to de-emulsify and form multiple phases, including an aqueous phase and a non-aqueous phase, the non-aqueous phase comprising:
 at least 15 weight percent surfactant,
 at least 5 weight percent plant material,
based on total weight non-aqueous phase.

33. A method of example 32 wherein the at least 15 weight percent surfactant is amide-based surfactant.

34. A method of example 32 or 33 wherein the non-aqueous phase comprises:
 from 15 to 70 weight percent amide-based surfactant,
 at least 20 weight percent lipophilic plant material dissolved in the solution,
based on total weight non-aqueous phase.

35. A method of any of examples 32 through 34 wherein the non-aqueous phase comprises not more than 20 weight percent water based on total weight non-aqueous phase.

36. A method of any of examples 31 through 35 comprising compressing the solid plant material using a two-stage auger.

37. A method for extracting a lipophilic plant material from a plant, comprising steps of:
 a) obtaining a plant or portion thereof comprising a lipophilic plant material;
 b) processing the plant in an aqueous composition, wherein the aqueous composition has a basic pH and comprises at least one surfactant;
 c) lowering the pH of the aqueous composition wherein the surfactant i) partially or fully loses its ability to emulsify lipophilic and hydrophilic components in the processed plant composition, ii) partially or fully disassociates with the lipophilic plant material, iii) is chemically cleaved into two or more surfactant by-product, or any combination of i)-iii); and
 d) partially or fully separating the surfactant from the lipophilic plant material.

38. The method of example 37, where, in step b), the pH of the aqueous composition is greater than about 9.

39 The method of example 38, where, in step b), the pH of the aqueous composition is in a range of about 10 to about 13.

40. The method of any of examples 37 through 39, wherein the surfactant is a non-ionic surfactant.

41. The method of any of examples 37 through 40, wherein the surfactant includes nitrogen, sulfur, or a combination thereof.

42. The method of any of examples 37 through 41, wherein the surfactant has the formula $R^1NR^2R^3$, wherein $R^1$ is a hydrocarbon-containing group, and $R^2$ and $R^3$ are independently selected from groups comprising both oxygen and carbon atoms.

43. The method of example 42, wherein $R^1$ is has an amount of carbon atoms in the range of 6-24, and $R^2$ and $R^3$ are independently selected from alkoxylate groups.

44. The method of example 42 or 43, wherein the surfactant is an alkylamine alkoxylate.

45. The method of any of examples 37 through 41, wherein the surfactant has the formula $R^4C(O)NR^5R^6$, wherein $R^4$, $R^5$, and $R^6$ are independently selected from saturated and unsaturated hydrocarbon-containing groups, and $R^4$, $R^5$, and $R^6$ have a total number of carbon atoms in the range of about 6-16.

46. The method of example 45 wherein the amide-based surfactant has the formula:

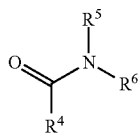

wherein $R^4$ is a saturated or unsaturated alkyl chain, $R^5$ and $R^6$ are the same or different and are saturated alkyl chains, and wherein $R^4$ has a greater number of carbon atoms than $R^5$ or $R^6$.

47. The method of example 46 wherein the amide-based surfactant is N, N-dimethyl 9-decenamide.

48. The method of any of examples 37 through 47, wherein the composition comprises a first surfactant and a second surfactant, wherein one or both of the first and/or second surfactant i) partially or fully loses its ability to emulsify lipophilic and hydrophilic components in the processed plant composition, ii) partially or fully disassociates with the lipophilic plant material, iii) is chemically cleaved into two or more surfactant by-product, or any combination of i)-iii).

48. The method of example 47, wherein the first surfactant has a different hydrophilic/lipophilic balance (HLB) than the second surfactant.

49. The method of example 48, wherein the first surfactant has a lower HLB than the second surfactant.

50. The method of any of examples 48 through 49, wherein the second surfactant is present in the composition in an amount (wt) greater than the first surfactant.

51. The method of any of examples 37 through 50 wherein the first surfactant is pH sensitive, and the second surfactant is cationic or anionic surfactant.

52. The method of any of examples 37 through 51, wherein the at least one surfactant is present in the composition in an amount in the range of about 0.1% (wt) to about 25% (wt), about 0.25% (wt) to about 20% (wt), about 0.5% (wt) to about 15% (wt), about 1% (wt) to about 10% (wt), about 1.5% (wt) to about 7.5% (wt), or 2% (wt) to about 5% (wt).

53. The method of any of examples 37 through 52 wherein the aqueous composition further comprises a water-immiscible solvent.

54. The method of example 53 wherein the water-immiscible solvent is hexane or propyl bromide.

55. The method of any of examples 37 through 54 wherein the aqueous composition further comprises a metal halide that facilitates precipitation of chlorophylls.

56(a). The method of any of examples 37 through 55, wherein the plant material is present in the composition in an amount in the range of about 0.1% (wt) to about 90% (wt), or preferably about 5% (wt) to about 60% (wt).

56(b). The method of any of examples 37 through 56(a), wherein step b) of processing comprises processing the plant using pressure, such as by using an auger, a sonicator, a macerator, a grinder, or a combination thereof.

57. The method of any of examples 37 through 56(b), comprising a step of removing one or more materials selected from the group consisting of plant fiber, colorants, chlorophylls, waxes, and fatty acids, between steps a) and d).

58. The method of any of examples 37 through 57, comprising a step of removing plant fiber between steps b) and c).

59. The method of any of examples 37 through 58, wherein step c) of lowering the pH comprises electrolytically lowering the pH, lowering the pH with one or more acids, or a combination thereof.

60. The method of any of examples 37 through 59, wherein step c) of lowering the pH results in a composition having a pH in the range of about 1 to about 7, or preferably about 3 to about 6.

61. The method of any of examples 37 through 60, wherein step d) comprises separating the surfactant from the lipophilic plant material using a centrifuge.

62. The method of any of examples 37 through 61, wherein the plant material comprises a cannabinoid.

63. The method of any of examples 37 through 62, wherein the plant or portion thereof is obtained from hemp, cannabis, hops, or citrus fruit or a rind thereof.

64. The method of any of the examples 37 through 63, wherein the surfactant mixture, after the lipophilic material, or part thereof, is removed, is reactivated, by raising the pH.

65. The method of example 64, wherein the pH is raised electrolytically.

66. The method of any of examples 37 through 65, wherein reactivated surfactant or some portion thereof is reused, or renters processing, one or more times, as described in example 37, step (b).

67. The method of any of examples 37 through 66, wherein the plant is treated with enzymes prior to processing.

68. The method of any of examples 37 through 67, wherein steam is injected prior to or during mechanical processing.

69. A system for extracting a lipophilic plant material from a plant, the system comprising:
  a) a plant processor cable of processing the plant using pressure, and in an aqueous composition comprising a surfactant;
  b) a pH-lowering feature, capable of lowering the pH in the aqueous composition; and
  c) a separator, capable of separating the surfactant from the lipophilic plant material.

70. A multi-stage auger as described, and a use of a multi-stage auger for removing liquid components from solid plant material.

71. A chemical extraction system as described comprising an electrolysis unit, and a method of processing a liquid composition using the electrolysis unit.

The invention claimed is:

1. A plant extract composition comprising:
   at least 15 weight percent surfactant, and
   at least 5 weight percent plant material, based on total weight of the plant extract composition; wherein the surfactant comprises each of:
   a pH-dependent surfactant comprising alkylamine alkoxylate surfactant, and
   an amide-based surfactant having the formula R4C(O)NR5R6, wherein R4, R5, and R6 are independently selected from saturated and unsaturated hydrocarbon-containing groups.

2. The plant extract composition of claim 1 comprising:
   from 15 to 70 weight percent surfactant, and
   at least 20 weight percent extracted lipophilic plant material that is dissolved, suspended, or emulsified within the plant extract composition, based on total weight of the plant extract composition.

3. The plant extract composition of claim 2 comprising:
   less than 5 weight percent oil different from oil in the extracted lipophilic plant material, based on total weight of the plant extract composition, cannabinoid plant material, based on total weight plant extract composition.

4. The plant extract composition of claim 1 comprising at least 5 weight percent cannabinoid plant material, based on total weight of the plant extract composition.

5. The plant extract composition of claim 1 comprising not more than 20 weight percent water based on total weight of the plant extract composition.

6. The plant extract composition of claim 1 wherein R4, R5, and R6 combined have a total number of carbon atoms in the range from 6-16.

7. The plant extract composition of claim 1 comprising:
   from 0.1 to 40 weight percent pH-dependent surfactant, and
   from 1 to 20 weight percent amide-based surfactant, based on total weight of the plant extract composition.

8. A method of extracting material from solid plant material, the method comprising:
   contacting solid plant material with liquid extraction medium comprising water, surfactant, and base, the surfactant comprising at least 0.1 weight percent pH-dependent surfactant based on total weight of the liquid extraction medium, and the liquid extraction medium having a basic pH; and
   after contacting the solid plant material with liquid extraction medium, lowering the pH of the liquid extraction medium to cause an emulsion of the liquid extraction medium to de-emulsify and form multiple phases, including an aqueous phase and a non-aqueous phase.

9. The method of claim 8 wherein the non-aqueous phase comprises:
   at least 15 weight percent surfactant,
   at least 1 weight percent cannabinoid, and
   not more than 20 weight percent water, based on total weight of the non-aqueous phase.

10. The method of claim 8 comprising:
    after lowering the pH of the liquid extraction medium, processing the liquid extraction medium to form a plant extract composition comprising:
    at least 15 weight percent surfactant,
    at least 1 weight percent cannabinoid, and
    not more than 20 weight percent water, based on total weight of the non-aqueous phase; and
    separating the cannabinoid from the plant extract composition by forming a liquid or solid phase that contains a concentrated amount of the cannabinoid.

11. A method for extracting a lipophilic plant material from a plant, comprising steps of:
    a) obtaining a plant or portion thereof comprising a lipophilic plant material;
    b) processing the plant or portion thereof in an aqueous composition, wherein the aqueous composition has a basic pH and comprises at least one surfactant;
    c) lowering the pH of the aqueous composition wherein the at least one surfactant: i) partially or fully loses its ability to emulsify lipophilic and hydrophilic components in the processed plant aqueous composition, or ii) partially or fully disassociates with from the lipophilic plant material, or iii) is chemically cleaved into two or more surfactant by-products, or any combination of two or more of 1)-iii); and
    d) partially or fully separating the at least one surfactant from the lipophilic plant material.

12. The method of claim 11, where, in step b): the pH of the aqueous composition in step b) is greater than about 9.

13. The method of claim 11, wherein the at least one surfactant comprises a non-ionic surfactant.

* * * * *